US012636393B1

(12) United States Patent
McDonald et al.

(10) Patent No.: US 12,636,393 B1
(45) Date of Patent: May 26, 2026

(54) AUTOMATED SYSTEMS FOR STERILITY TESTING OF PHARMACEUTICAL FLUID PRODUCTS

(71) Applicant: Automated Systems of Tacoma, LLC, Tacoma, WA (US)

(72) Inventors: Jordan McDonald, Bonney Lake, WA (US); Steven Ng, Kent, WA (US); Michael Moore, Gig Harbor, WA (US); Raul A. Passarini, Edgewood, WA (US)

(73) Assignee: Automated Systems of Tacoma, LLC, Tacoma, WA (US)

( * ) Notice: Subject to any disclaimer, the term of this patent is extended or adjusted under 35 U.S.C. 154(b) by 0 days.

(21) Appl. No.: 18/945,267

(22) Filed: Nov. 12, 2024

(51) Int. Cl.
| | |
|---|---|
| *G01N 33/15* | (2006.01) |
| *A61L 2/28* | (2006.01) |
| *G01N 35/00* | (2006.01) |
| *G01N 35/10* | (2006.01) |

(52) U.S. Cl.
CPC ................ *A61L 2/28* (2013.01); *G01N 33/15* (2013.01); *G01N 35/00584* (2013.01); *G01N 35/1079* (2013.01); *G01N 2035/00277* (2013.01); *G01N 2035/1053* (2013.01)

(58) Field of Classification Search
CPC .... A61L 2/28; G01N 33/15; G01N 35/00584; G01N 35/0099; G01N 35/02; G01N 35/026; G01N 35/1079; G01N 2035/00277; G01N 2035/0405; G01N 2035/0412; G01N 2035/0413; G01N 2035/0415; G01N 2035/1053; Y10T 436/113332

USPC ................ 422/560–562, 570; 436/1, 47, 177
See application file for complete search history.

(56) References Cited

U.S. PATENT DOCUMENTS

| | | | | |
|---|---|---|---|---|
| 2,562,815 | A | * | 7/1951 | Oscroft ................... B65B 3/003 |
| | | | | 141/181 |
| 3,965,642 | A | * | 6/1976 | Hills ....................... B65B 61/06 |
| | | | | 53/550 |
| 4,036,698 | A | * | 7/1977 | Bush ........................ C12Q 1/22 |
| | | | | 435/31 |

(Continued)

FOREIGN PATENT DOCUMENTS

| | | |
|---|---|---|
| CN | 109813575 B | 5/2019 |
| CN | 113462545 A | 10/2021 |

(Continued)

OTHER PUBLICATIONS

D'Arbeloff, N. C., Drug Development and Industrial Pharmacy 1988, 14, 2733-2740. (Year: 1988).*

(Continued)

*Primary Examiner* — Arlen Soderquist
(74) *Attorney, Agent, or Firm* — Bamert Regan PLLC

(57) ABSTRACT

The present invention discloses an automated sterility testing assembly that has a needle holder sized and configured to selectively retain a needle fluidly coupled to a sterility testing filter. The holder is configured to move the needle in a first direction to pierce selected containers disposed on a carrier and to move the needle in a second direction opposite the first direction to remove the needle from the selected containers. The assembly includes a brace that braces the fluid containers during their respective piercings by the needle. Accordingly, the brace prevents the needle from moving the fluid containers out of the carrier.

26 Claims, 19 Drawing Sheets

(56) References Cited

U.S. PATENT DOCUMENTS

| | | | | |
|---|---|---|---|---|
| 4,292,405 A * | 9/1981 | Mascoli | B01D 63/00 | 435/31 |
| 4,351,900 A * | 9/1982 | Lemonnier | C12M 33/04 | 435/31 |
| 4,610,670 A * | 9/1986 | Spencer | B29C 66/5221 | 604/905 |
| 4,640,777 A * | 2/1987 | Lemonnier | B29C 66/542 | 210/455 |
| 4,805,821 A | 2/1989 | Kowalczyk et al. | | |
| 5,213,967 A * | 5/1993 | Erdman | A61L 2/28 | 435/31 |
| 5,216,926 A * | 6/1993 | Lipscomb | G01N 35/1079 | 73/864.22 |
| 5,569,181 A * | 10/1996 | Heilman | A61M 5/007 | 604/30 |
| 5,579,928 A * | 12/1996 | Anukwuem | B01L 9/06 | 422/561 |
| 5,609,826 A * | 3/1997 | Cargill | C07H 21/00 | 422/570 |
| 5,674,741 A * | 10/1997 | Watanabe | B29C 66/1142 | 156/503 |
| 2001/0053335 A1* | 12/2001 | Hashimoto | G01N 35/0099 | 422/65 |
| 2003/0054331 A1* | 3/2003 | Fraser | A01N 1/162 | 435/2 |
| 2003/0143120 A1* | 7/2003 | Ruediger | C40B 60/14 | 422/561 |
| 2003/0215365 A1* | 11/2003 | Sevigny | G01N 35/025 | 422/562 |
| 2005/0048598 A1* | 3/2005 | Guenec | A61L 2/28 | 435/31 |
| 2005/0221417 A1 | 10/2005 | Houghton et al. | | |
| 2010/0291619 A1* | 11/2010 | Robinson | G01N 35/0099 | 435/288.7 |
| 2010/0291669 A1* | 11/2010 | Robinson | G01N 35/0099 | 901/14 |
| 2011/0172810 A1* | 7/2011 | Mlodzinski | G07F 11/1657 | 250/455.11 |
| 2012/0051987 A1* | 3/2012 | Johnson | B01L 9/06 | 422/562 |
| 2012/0222774 A1* | 9/2012 | Husnu | B65B 37/06 | 141/69 |
| 2017/0029760 A1* | 2/2017 | Niu | C12M 33/18 | |
| 2017/0051331 A1* | 2/2017 | Olivier | G01N 1/4077 | |
| 2017/0128675 A1* | 5/2017 | Koike | A61J 1/20 | |
| 2017/0319728 A1* | 11/2017 | Schmitz | A61L 2/20 | |
| 2017/0321244 A1* | 11/2017 | Verma | G21G 1/001 | |
| 2018/0257051 A1* | 9/2018 | De Haan | B01F 33/844 | |
| 2018/0298419 A1 | 10/2018 | Ronsick et al. | | |
| 2019/0371584 A1* | 12/2019 | Carney | H01J 49/40 | |
| 2020/0319219 A1* | 10/2020 | Vansickler | G01N 35/00732 | |
| 2021/0380924 A1 | 12/2021 | Huang et al. | | |
| 2023/0285242 A1* | 9/2023 | Shem-Tov | A61J 1/1406 | |
| 2024/0209411 A1 | 6/2024 | Pruehl et al. | | |

FOREIGN PATENT DOCUMENTS

| | | | |
|---|---|---|---|
| CN | 114717103 A | | 7/2022 |
| CN | 117025377 A | | 11/2023 |
| DE | 3012085 A | * | 10/1981 |
| JP | 63230077 A | * | 9/1988 |

OTHER PUBLICATIONS

Remazeilles, A et al., In "Robot 2022" Tardioli, D. et al. (Eds.), 2023, LNNS 589, 223-234. (Year: 2023).*

Nicholas C. D'arbeloff, "Improving the Integrity of Pharmaceutical Sterility Testing: A New Robotic Approach", Published: Oct. 20, 2008, Abstract only submitted.

* cited by examiner

AUTOMATED SYSTEMS FOR STERILITY TESTING OF PHARMACEUTICAL FLUID PRODUCTS

FIELD OF THE INVENTION

The invention relates generally to sterility testing and, more particularly, to automated sterility testing of pharmaceutical products.

BACKGROUND OF THE INVENTION

Sterile products, such as injected medications, are produced in environments where significant steps are taken to maintain sterility. However, sterile products can still be contaminated in these environments. Accordingly, sterility testing is performed on selections of the products, typically in batches, to confirm that the products are sterile.

Sterility testing is typically performed manually by an operator with a test kit. FIG. 1 shows a sterility test kit 32 for manual testing by an operator. The test kit 32 has a needle 34, a pair of test canisters such as membrane filtration canisters 36, or containers, with respective filters 37, a pair of tubes 38 extending from the needle 34 to the test canisters 36, pinchers 40 such as pinch clamps, tube clamps, or FTM on each of the tubes 38 that enable the operator to selectively restrict fluid flow through the tubes 38, three bottles of wetting fluid 42 that are typically provided separate from the test kit 32, and two bottles of growth media 44. The growth media 44 typically includes aerobic media in one bottle and anaerobic in another bottle. The test kit 32 is generally used by an operator in a sterile chamber where the operator can manipulate the items in the test kit 32 via gloves attached to a wall of the sterile chamber and extending into the sterile chamber. The operator follows a procedure having the following steps of: (1) inserting the needle 34 into the bottles of wetting fluid 42 to wet the filters in each of the test canisters 36, which typically have volumes specified by a standard such as USP 71; (2) inserting the needle 34 into the test samples 46 one at a time to drain the sample fluid through the filters 37 of the test canisters 36; (3) rinsing the containers 36 with 300 mL each from wetting containers 42 (4) plugging an outlet 39 on each of the test canisters 36; (5) pinching one of the pinchers 40 and draining the aerobic growth media 44 into one of the test canisters 36 for which the tube 38 is not pinched; (6) un-pinching the pincher 40 and pinching the other pincher 40, then draining the anaerobic growth media 44 into the other of the test canisters 36 for which the tube 38 is not pinched; (7) both tubes 38 are pinched 40 at side closest to the canisters 36; (8) the tube 38 is manually cut between the pinchers (or FTM's) and the canister 36; and (9) the now cut tube 38 is manually looped to close or seal container 36 through port 170. Following filling of the test canisters 36, the test canisters 36 can be sent off for testing, specifically, observation of bacteria growth on the filter. This approach has been known as a longstanding problem in the industry. In particular, this approach causes major delays in the manufacturing process because it consumes a significant portion of the operators' time. Moreover, manual operation of the test kit 32 creates the opportunity for the sterile environment to be breached if the operator accidentally pricks the gloves and thereby enable air to flow from the environment outside the sterile chamber into such chamber.

One attempt to automate sterility testing is described in U.S. Pre-Grant Publication No. 2021/0380924. This application is directed to a bacteria collection system that reduces operator involvement in the sterility testing process. However, this system has undesirable complexities such as the testing bottles requiring a flipping mechanism for grabbing the bottles, flipping the bottles upside-down, and moving the bottles to the needle. The placement of the bottles on a tray that is unitary with the automation equipment creates difficulties with sterilization of the bottles, tray, and equipment because everything must be sterilized with each use, but a sterilization fluid cannot contact the space between the tray and bottles. The operator must therefore be involved in the sterilization step. Additionally, movement of the bottles to the needle before rotation increase the steps and time required to perform sterility testing.

For these reasons, there is a need for automated sterility testing where the test kit can be easily sterilized. There is also a need for automated sterility testing that can be performed with fewer steps and reduced operator involvement. There is a further need for automated sterility testing that reduces the likelihood of breach of the sterile environment.

SUMMARY OF THE INVENTION

It is therefore an object of the present invention to provide sterility testing assemblies that provide the ability to test the sterility of product samples with reduced operator involvement.

It is also an object of the present invention to provide sterility testing assemblies that achieve the above object and that also decrease the time required for performing sterility testing.

It is another object of the present invention to provide sterility testing assemblies that achieve the above objects and that also reduce the error rate in sterility testing.

The invention achieves the above objects, as well as other objects and advantages that will become apparent from the description that follows, by providing sterility testing assemblies that have a needle holder configured to selectively retain a needle fluidly coupled to a sterility testing filter. The holder is configured to pierce respective closures of a fluid containers disposed on a carrier. The holder is configured to remove the needle from the respective closures. The assemblies preferably further include at least one pump configured to draw fluid through the respective closures and a filter in a test container after the needle pierces the respective closures. A brace preferably braces the plurality of fluid containers during piercing the respective closures by the needle. The brace preferably prevents the needle from moving the fluid containers out of the carrier. In some embodiments, a seal actuator is configured to selectively seal with a vent sealer a vent port of the test container during filling of the test container with liquid from the fluid containers or draining the liquid from the test container. A tube sealer is in some embodiments configured to seal tubing extending between the needle holder and the test container. A cutter is in some embodiments configured to cut the tubing between the seal and the needle holder. Sealing and cutting of the tubing according to those embodiments enables removal of the test container while contents of the test container are sealed.

In some embodiments, a plug holding arm is configured to selectively hold a plug for the test container. The plug holding arm is preferably configured to insert the plug into the vent of the test container after draining a growth media from a container of the plurality of fluid containers into the test container. The plug holding arm is preferably further configured to release the plug after inserting the plug into the vent of the test container.

In some embodiments, a plug holding arm is configured to selectively hold a plug for the test container. The plug holding arm is preferably configured to insert the plug into a fluid outlet of the test container before draining a bacterial growth media from one of the fluid containers into the test container. The plug holding arm is preferably configured to release the plug after inserting the plug into the fluid outlet of the test container.

In some embodiments, a processor to determines that one or more pumps completed drawing the pharmaceutical fluid into the test container. At least one pump preferably draws a rinsing fluid from one of the containers into the test container based on the determination that the one or more pumps completed drawing the pharmaceutical fluid into the test container.

In some embodiments, a conveyor is configured to move the carrier in the assembly, and a vertical actuator is configured to lift the carrier off the conveyor during a decontamination process.

In some embodiments, a drain actuator is configured to selectively couple a drain adaptor to a fluid outlet of the test container to enable one or more pumps to drain the liquid from the test container through the fluid outlet and to enable coupling a plug to the fluid outlet of the test container after separation of the drain adapter from the fluid outlet.

In some embodiments, the carrier has a plurality of retainers sized and dimensioned to retain the plurality of fluid containers. Each of the plurality of retainers preferably have one or more prongs that provide reduced contact with the fluid containers compared to a holder that provides contact with a continuous region of each of the plurality of fluid containers about perimeters of the plurality of fluid containers.

In some embodiments, the one or more prongs of each of the retainers include at least three prongs spaced apart to circumferentially surround a respective one of closure-receiving spaces defined by the carrier. The closure-receiving spaces is preferably sized and dimensioned to receive respective closures of the fluid containers. The needle holder is preferably configured to move the needle to pierce a selected one of the closures while the selected closure is disposed in one of the closure-receiving spaces.

In some embodiments, the retainers are arranged in at least one row and a plurality of columns, and the needle holder is configured to move the needle into the closure-receiving spaces in a predetermined order.

In some embodiments, the brace complements a profile defined by the fluid containers such that the brace simultaneously contacts each of the fluid containers. In some embodiments, the brace is configured to contact the fluid containers before the needle holder moves the needle to pierce the selected closure.

In some embodiments, a pincher is configured to selectively restrict fluid flow through tubing fluidly coupling the needle and the test container.

In some embodiments, a tube sealer is configured to seal tubing fluidly coupling the needle holder and the test container. A cutter is preferably configured to cut the tubing between the seal and the needle holder. Sealing and cutting of the tubing according to such embodiment enables removal of the test container while contents of the test container are sealed.

In some embodiments, the needle is moved with an actuator to pierce a rinsing-fluid container. The rinsing fluid is preferably drawn into the first test container after drawing the pharmaceutical fluid from the second container into the first test container. In some embodiments, after the draining the rinsing fluid, the needle is moved with an actuator to pierce a growth-media container. In some embodiments, a growth media is drained, through the needle and from the growth-media container, into the first test container. In some embodiments, both the first and second container contain a pharmaceutical fluid to be tested, and the first container contains an aerobic or anaerobic growth media while the second container contains the other of the aerobic or anaerobic growth media.

In some embodiments, an actuator pinches first tubing that fluidly couples the needle to the first test container and thereby restricts fluid flow from the second container to the first test container. In some embodiments, fluid from the second container is thereafter pumped, through the needle and while the first tubing is pinched, to a second test container. In some embodiments, the actuate un-pinches the first tubing and thereby enables flow from the second container to the first test container. In some embodiments, pinching with an actuator the second tubing restricts fluid flow from the second container to the second test container, thereby enabling pumping, through the needle and while the second tubing is pinched, fluid from the second container to the first test container.

In some embodiments, an actuator unseals a vent port of the first test container, thereby enabling filling the first test container with an aerobic or anaerobic growth media while the vent port is unsealed. In some embodiments, an actuator couples a plug to a fluid outlet of the first test container after filling the first test container with the growth media.

In some embodiments, an actuator removes a sheath from the needle before piercing one of the containers.

BRIEF DESCRIPTION OF THE DRAWINGS

The preferred embodiment of the present invention is described in detail below with reference to the following drawings.

5

Figure 5A:
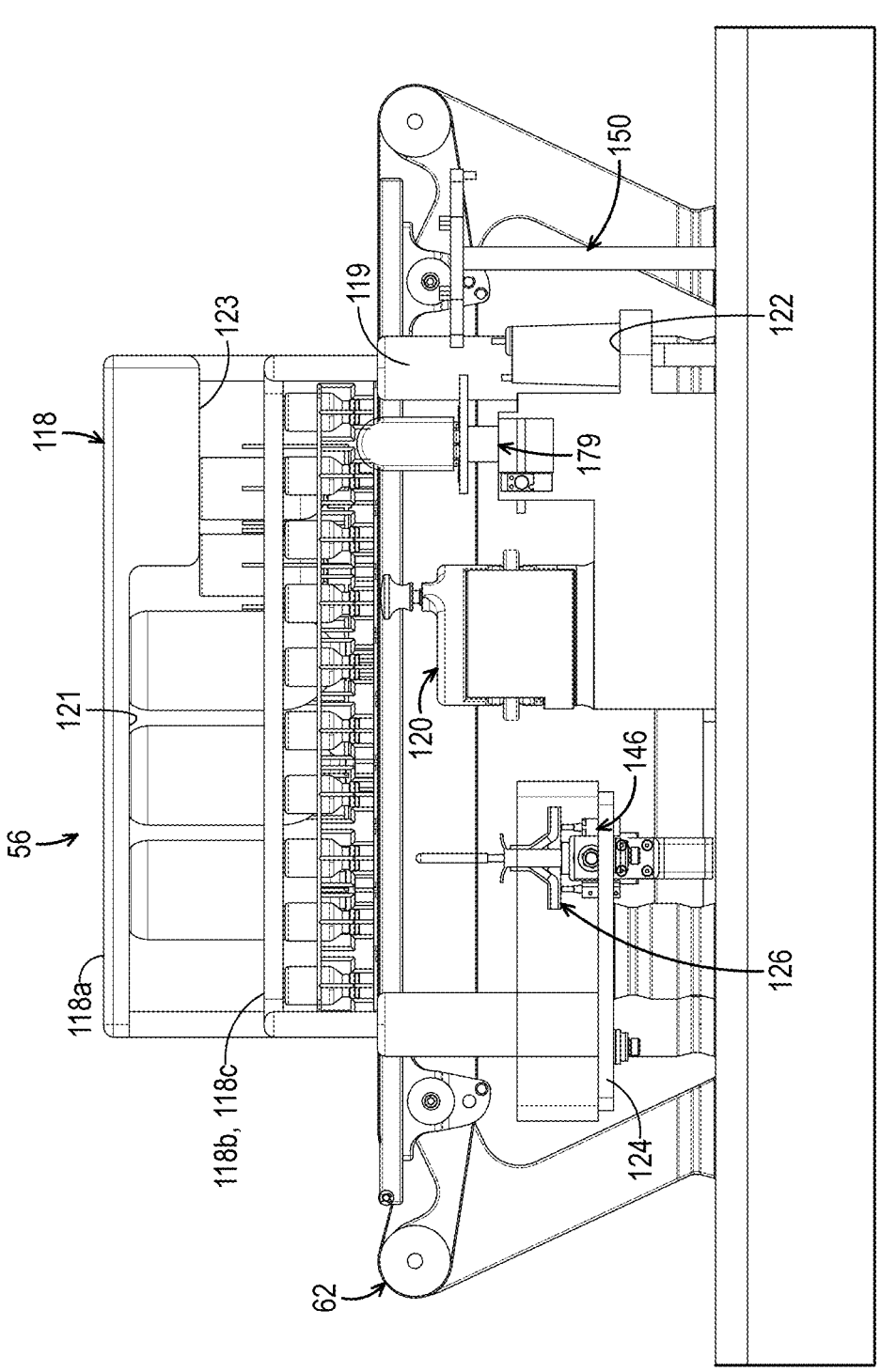
FIG. 5A is an isometric front elevation view of a sterility testing chamber for the sterility testing assembly of FIG. 2A.
Figure 5B:
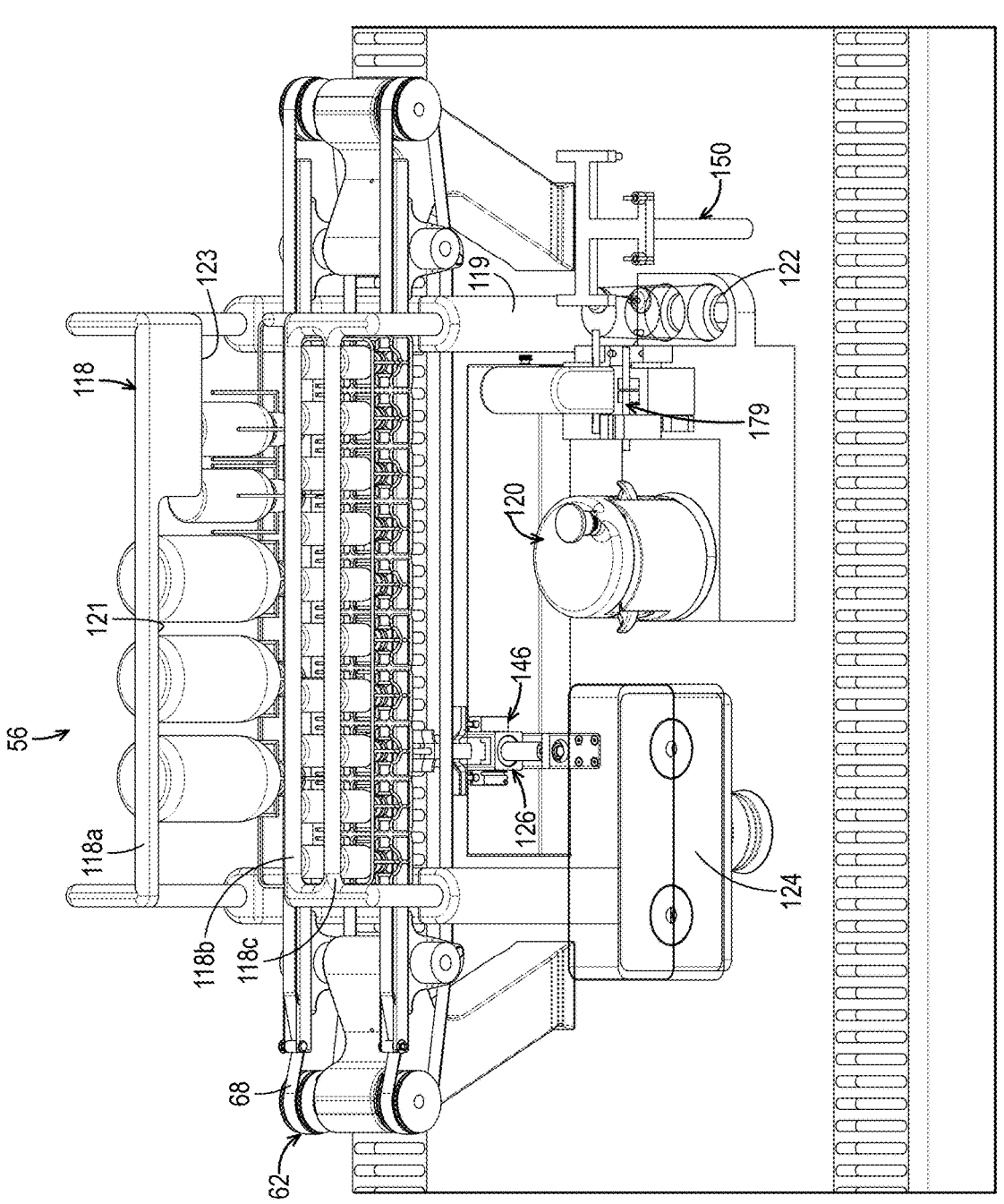
FIG. 5B is an isometric front perspective view of the sterility testing chamber of FIG. 5A.
Figure 5C:
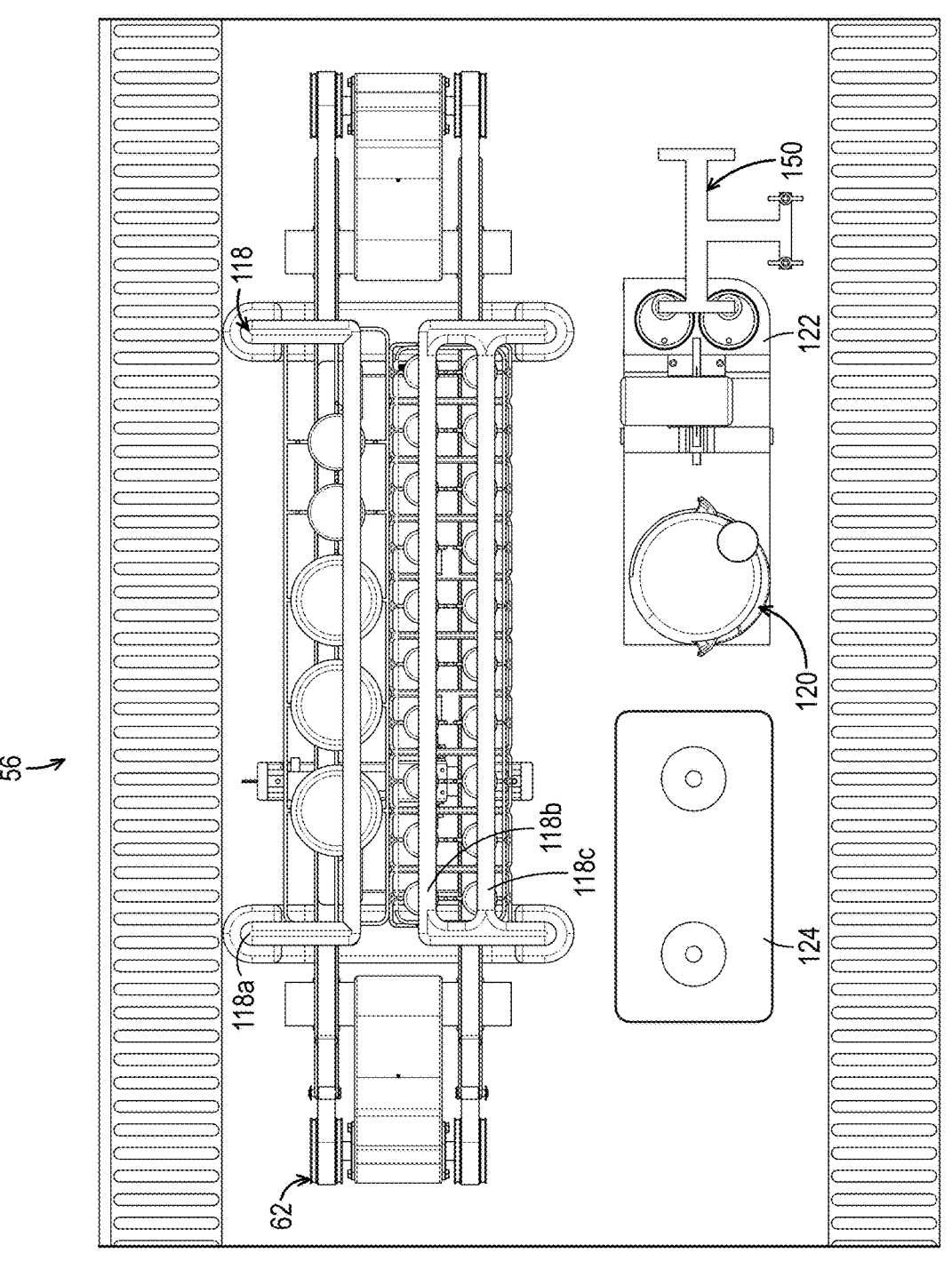
FIG. 5C is an isometric top plan view of the sterility testing chamber of FIG. 5A.
Figure 5D:
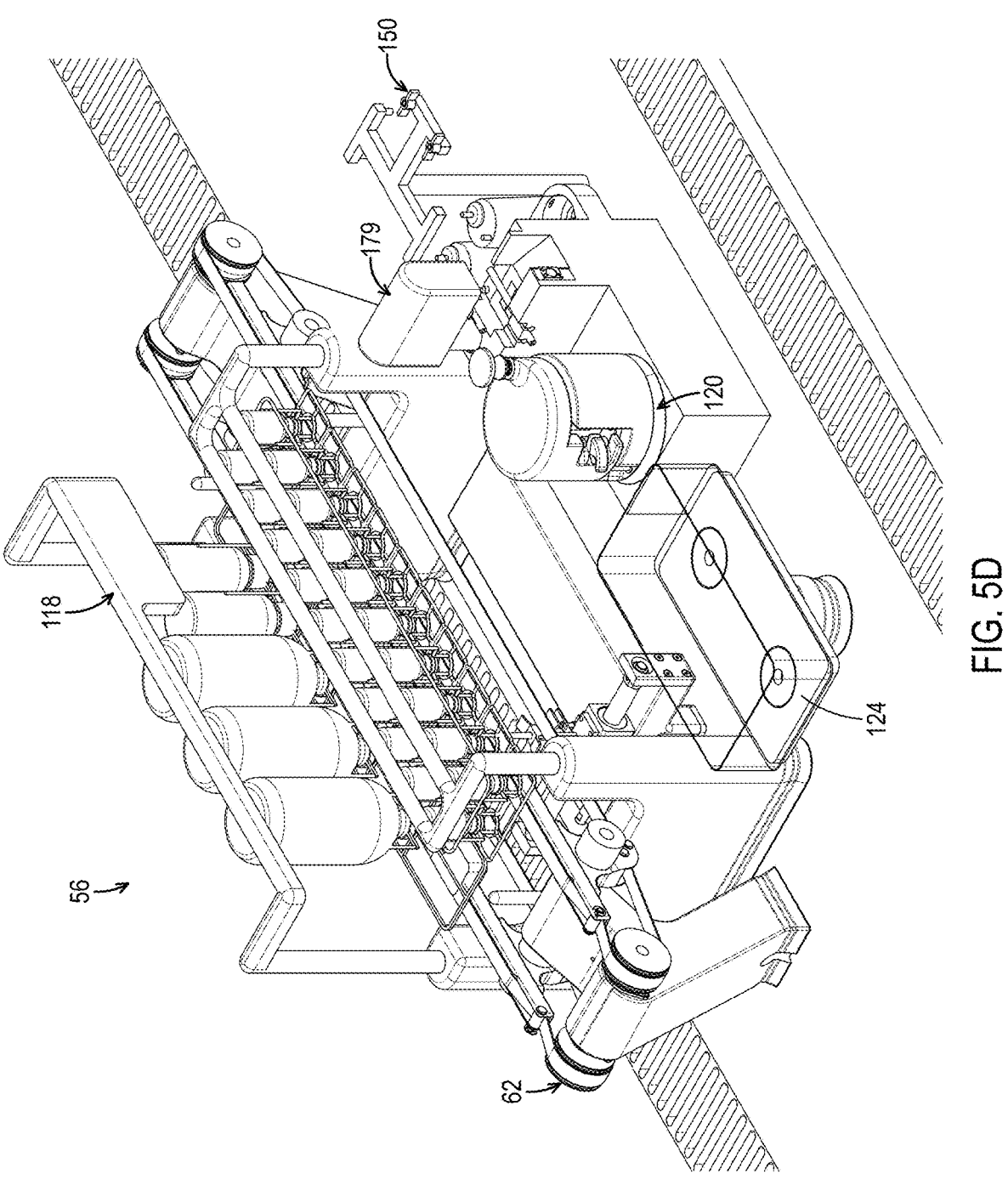
FIG. 5D is an isometric perspective view of the sterility testing chamber of FIG. 5A.
Figure 9:
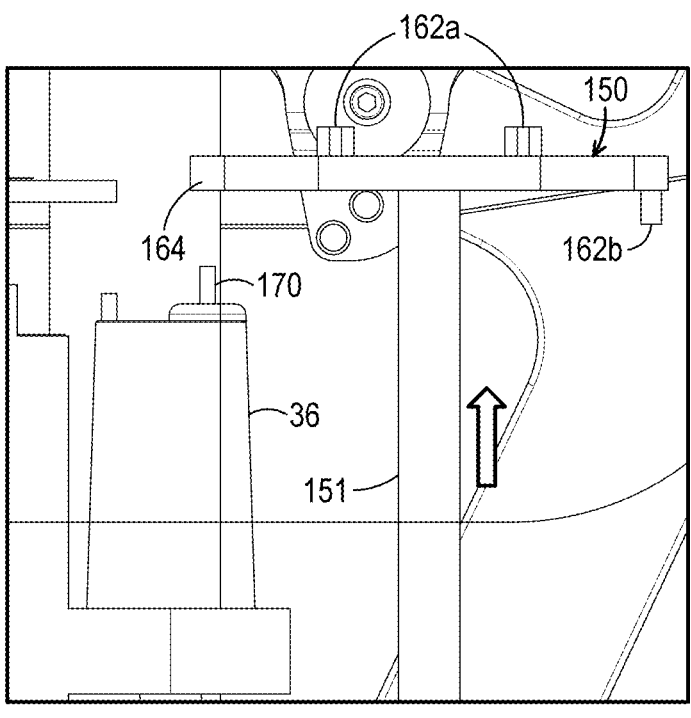
Figure 10:
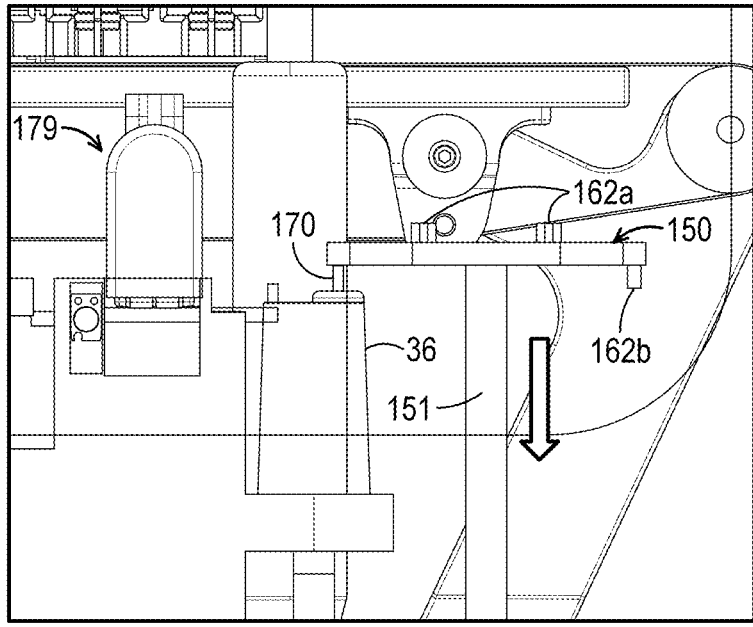

FIGS. 9 and 10 are partial front elevation views of a canister plug holding arm in the sterility testing chamber of FIG. 5A.

Figure 1:
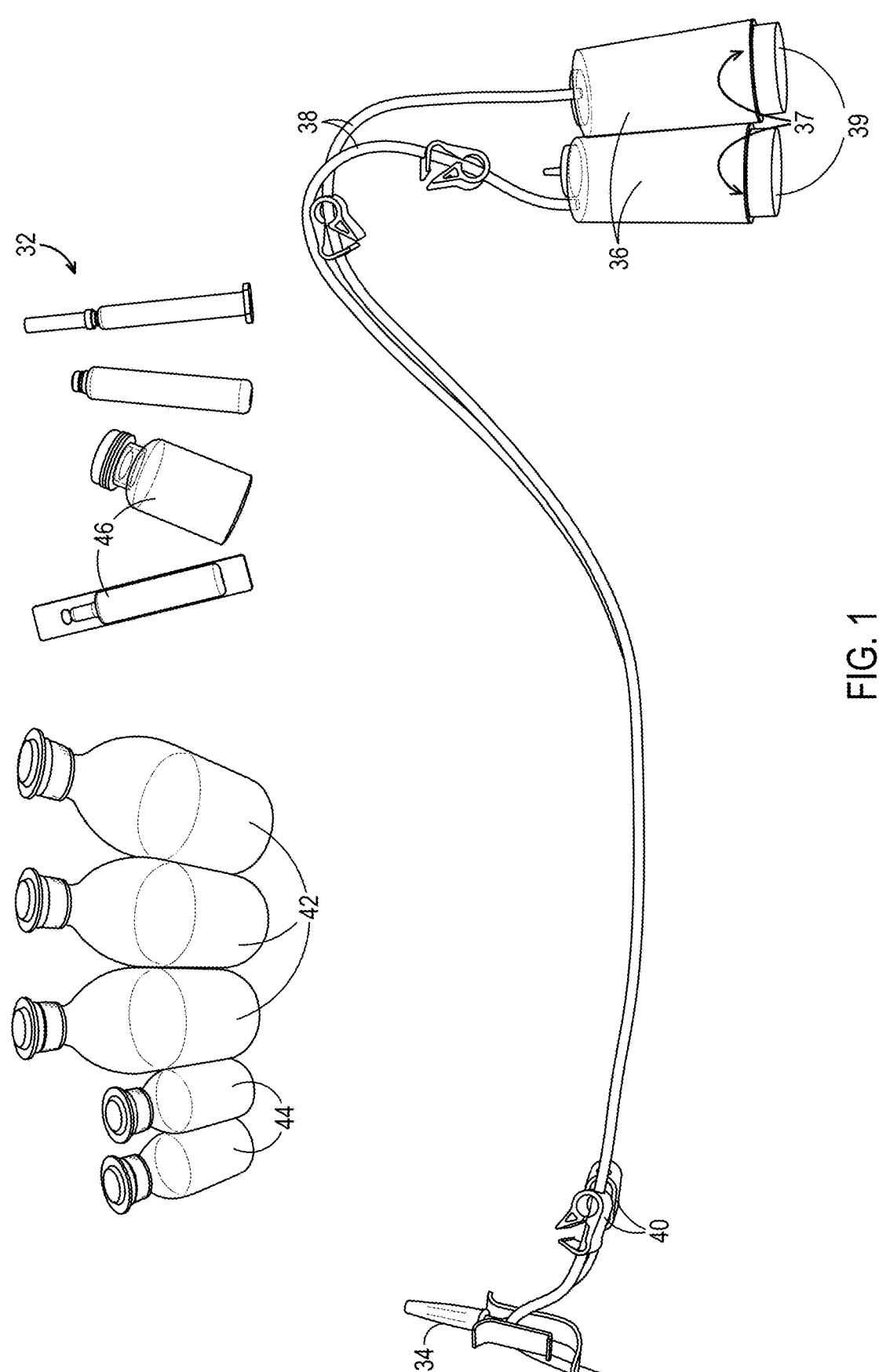
FIG. 1 is a front perspective view of a sterility test kit.
Figure 2A:
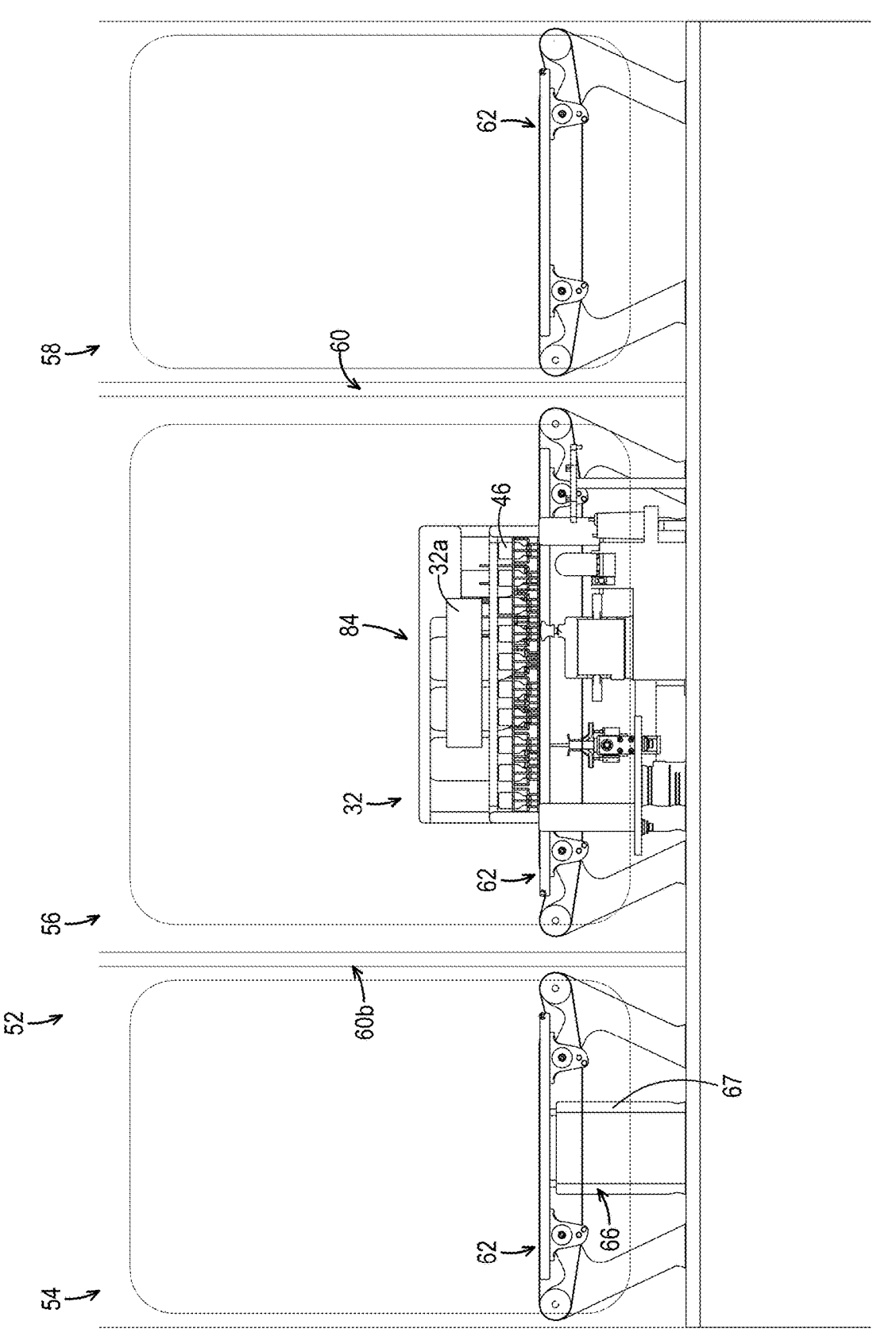
FIG. 2A is a front elevation view of a sterility testing assembly.
Figure 11:
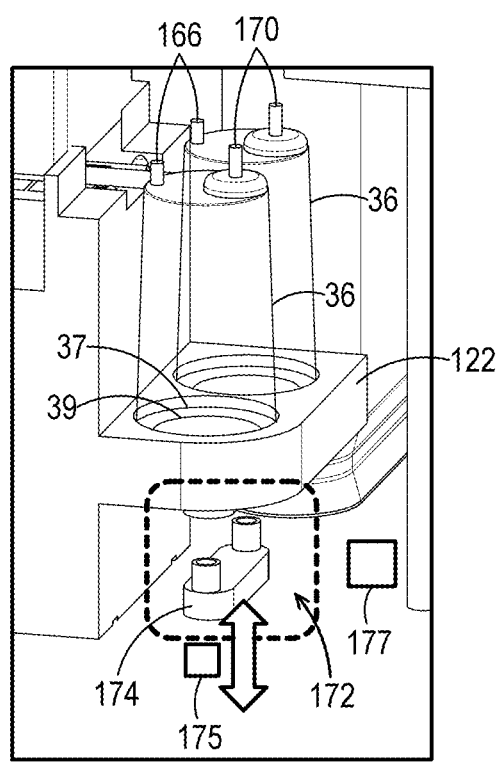
Figure 12:
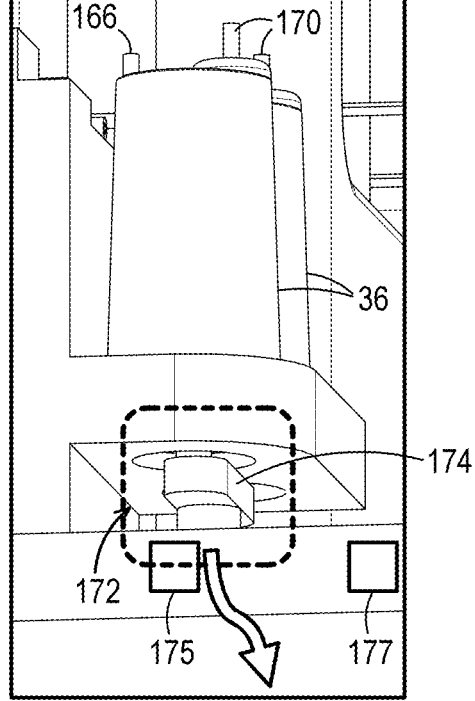

FIGS. 11 and 12 are partial front isometric perspective views of a drain assembly for the sterility testing assembly of FIG. 2A.

Figure 13:
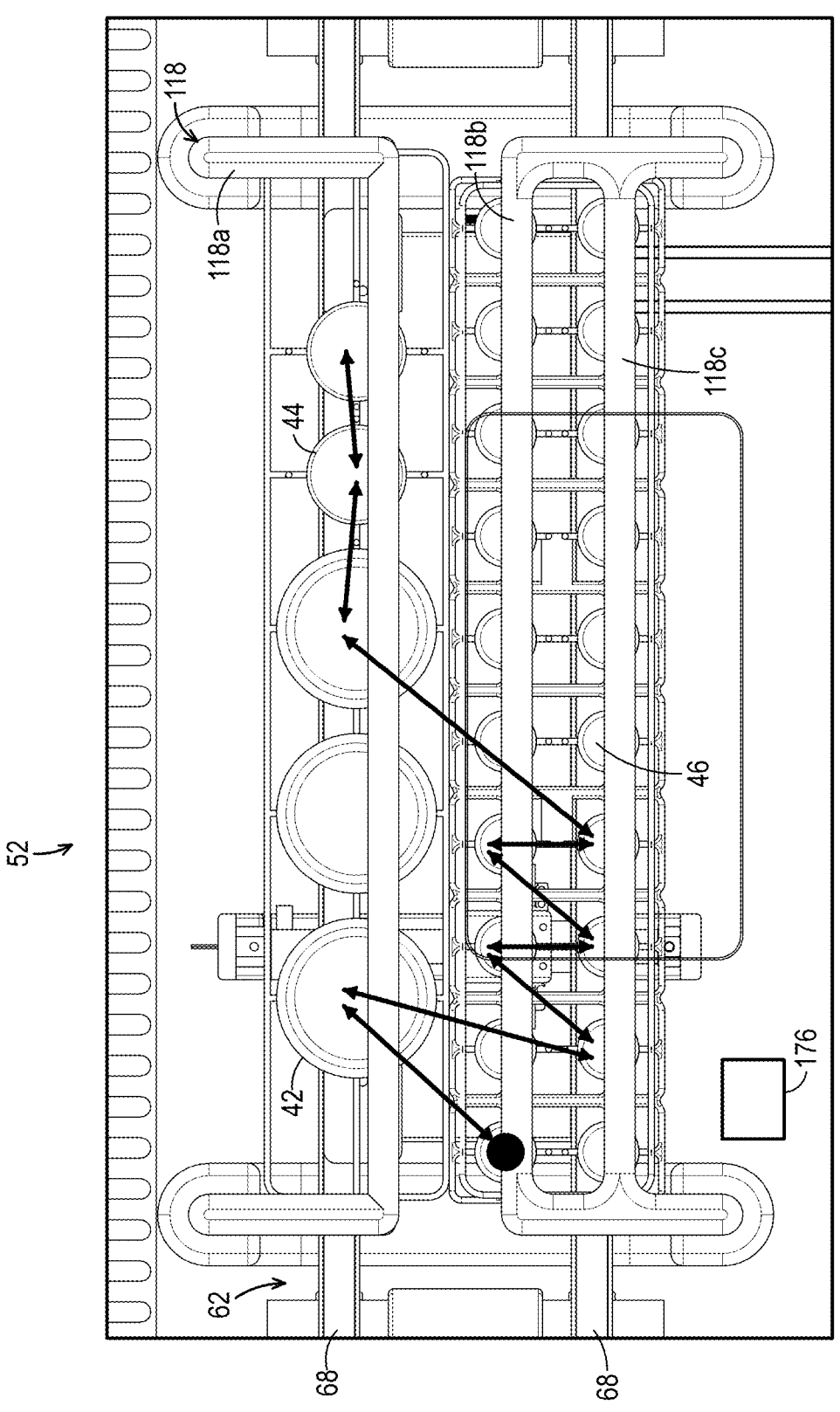

FIG. 13 is a partial top plan view of a path of travel of the needle control assembly through the sterility testing chamber of FIG. 5A.

Figure 14A:
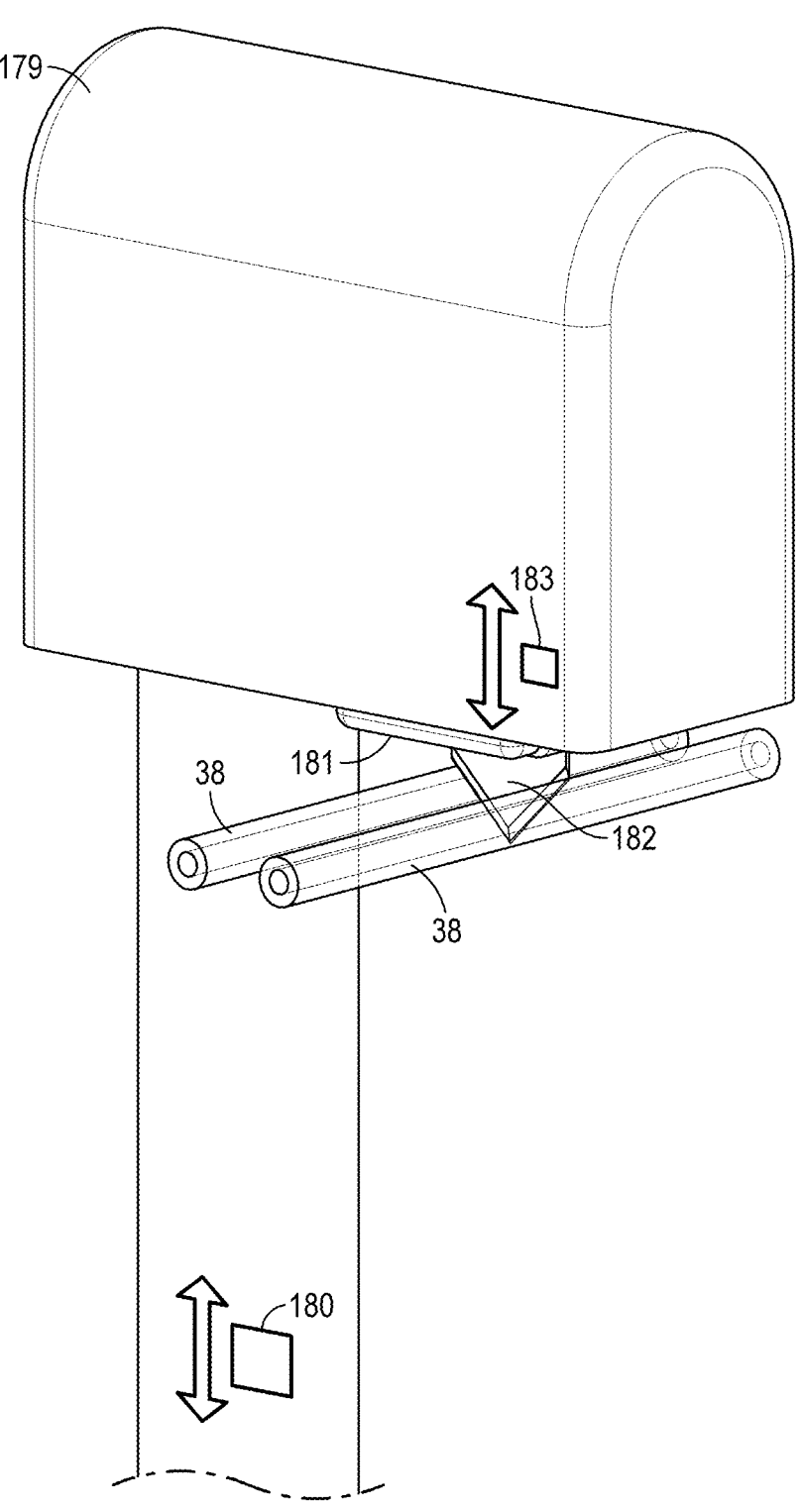

FIG. 14A is a partial isometric perspective view of a cutting and sealing station for the sterility testing chamber of FIG. 5A.

Figure 14B:
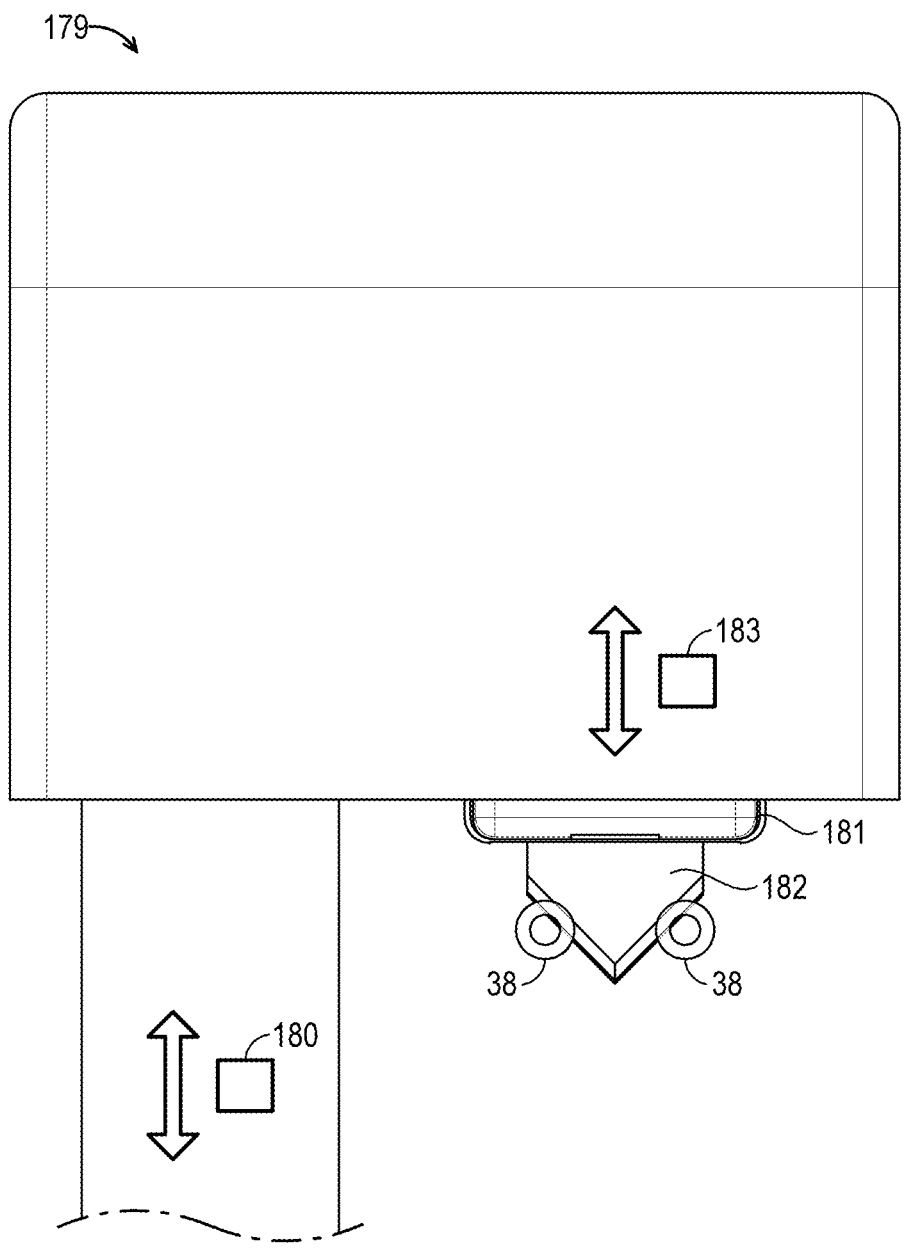

FIG. 14B is a partial elevational side view of the cutting and sealing station of FIG. 14A.

Figure 15:
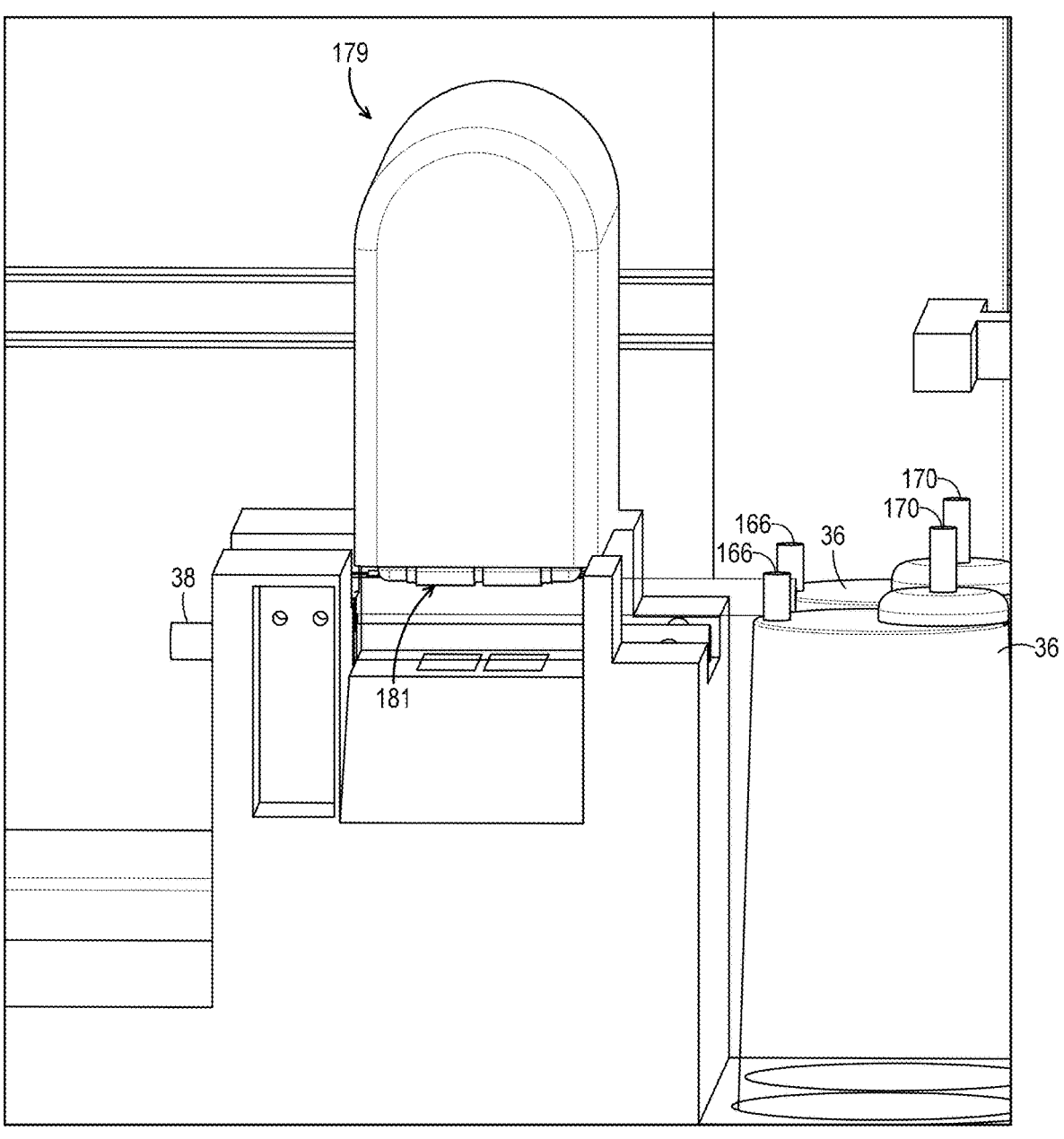

FIG. 15 is another perspective view of the cutting and sealing station of FIGS. 14A and 14B.

Figure 16:
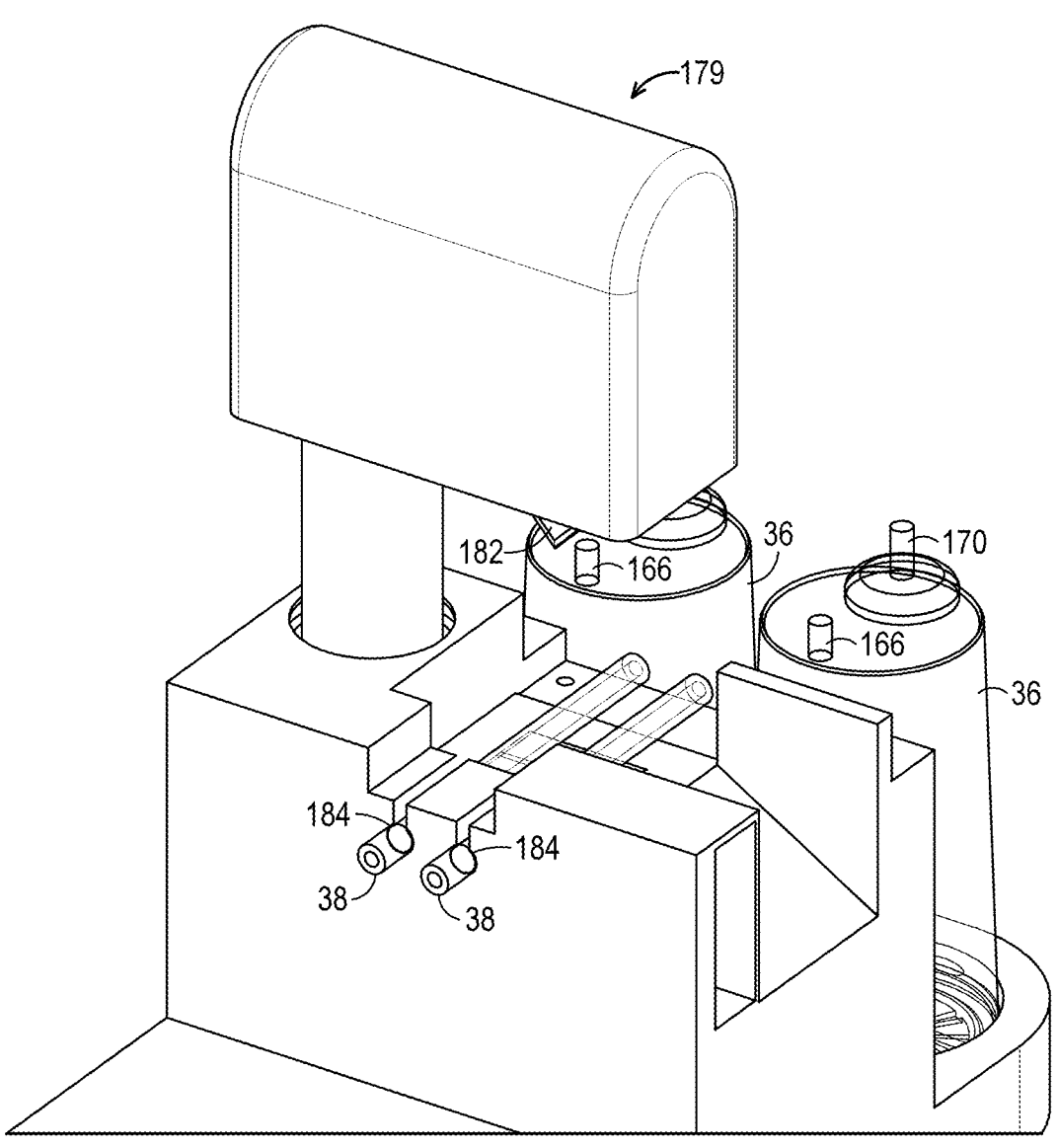

FIG. 16 is a partial isometric perspective view of the cutting and sealing station of FIGS. 14A and 14B.

DETAILED DESCRIPTION OF THE PREFERRED EMBODIMENT

An automated sterility tester assembly in accordance with the principles of the invention is generally indicated at reference number 52 in the Figures of the attached drawings, wherein numbered elements in the Figures correspond to like numbered elements herein.

Figure 2B:
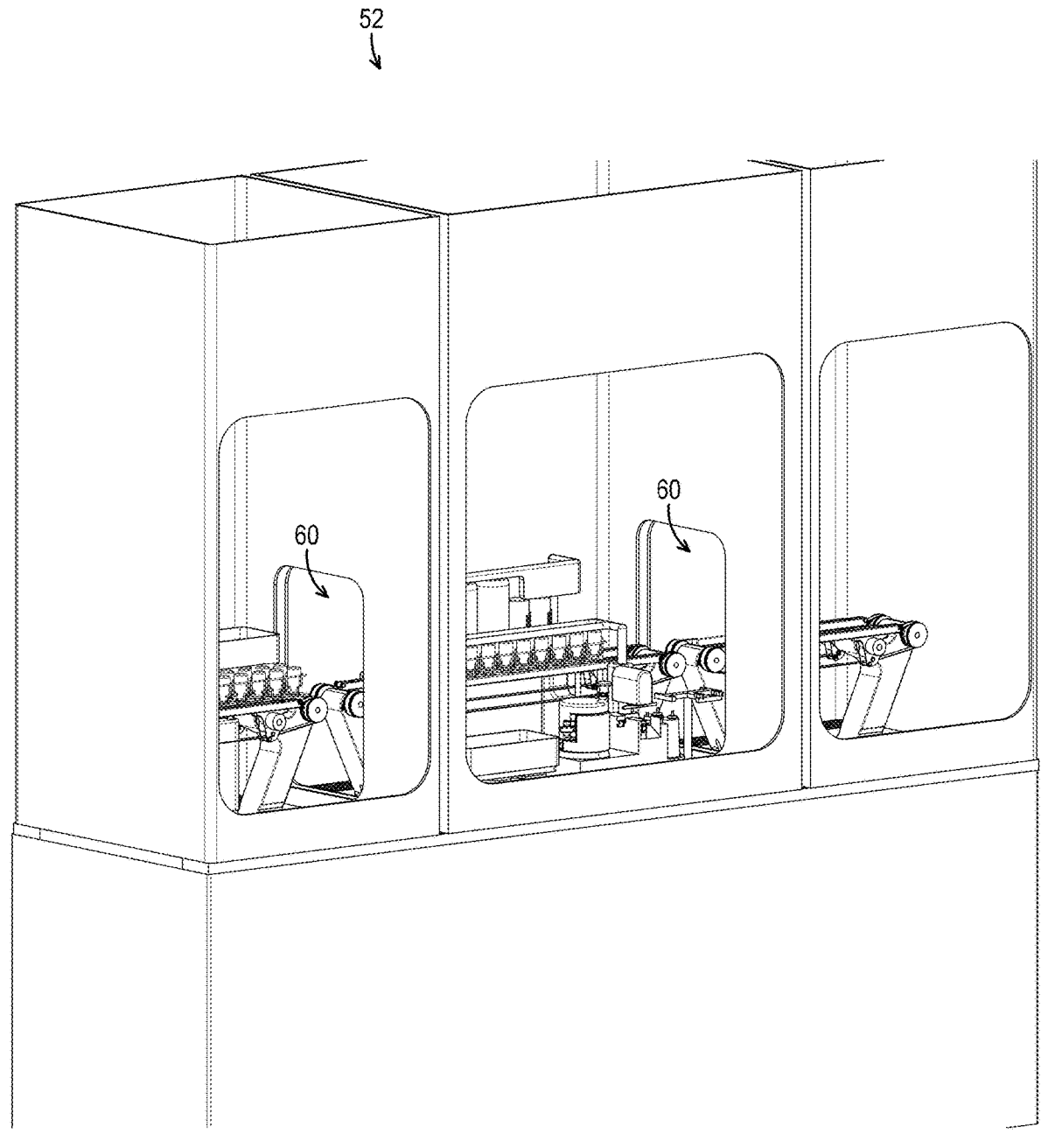
FIG. 2B is an isometric perspective view of the sterility testing assembly of FIG. 2A.

Referring now to FIG. 2A, FIG. 1, FIG. 5, and FIG. 10, an automated sterility tester assembly 52 is depicted as having an infeed pass chamber 54, a sterility testing chamber 56, and an outfeed pass chamber 58. Each of the infeed pass chamber 54, the sterility testing chamber 56, and the outfeed pass chamber 58 has a respective door 60 that selectively isolates it from the adjacent chamber and preferably has a respective conveyor 62 for transferring the sterility test kit 32 and holders 84 from the infeed pass chamber 54 through the sterility testing chamber 56 and to the outfeed pass chamber 58. As shown in both FIGS. 2A and 2B, the doors 60 between the adjacent chambers may be selectively opened to permit the sterility test kit 32 to pass through each of the chambers and may additionally be selectively closed to isolate the test chamber for maintaining a sterile environment. Moreover, the assembly 52 preferably removes the sheath 144 of the needle of the test kit 32, selectively pierces the containers 42, 44 of the kit 32 and samples 46 to be tested without removing the containers from a nest 84 in which they were delivered into the test chamber 56, selectively plugs respective vent ports 170 of test containers such as membrane filtration canisters or other filter containers 36 to wet and expose the filters 37 of those containers 36 to the samples to be tested, and plugs the containers 36 for delivery to a testing facility, all without operator involvement. Accordingly, the invention described herein facilitates a sterile environment with limited operator intervention to limit possible sources of contamination and thereby reduce the resulting error rate of sterility testing.

Figure 3:
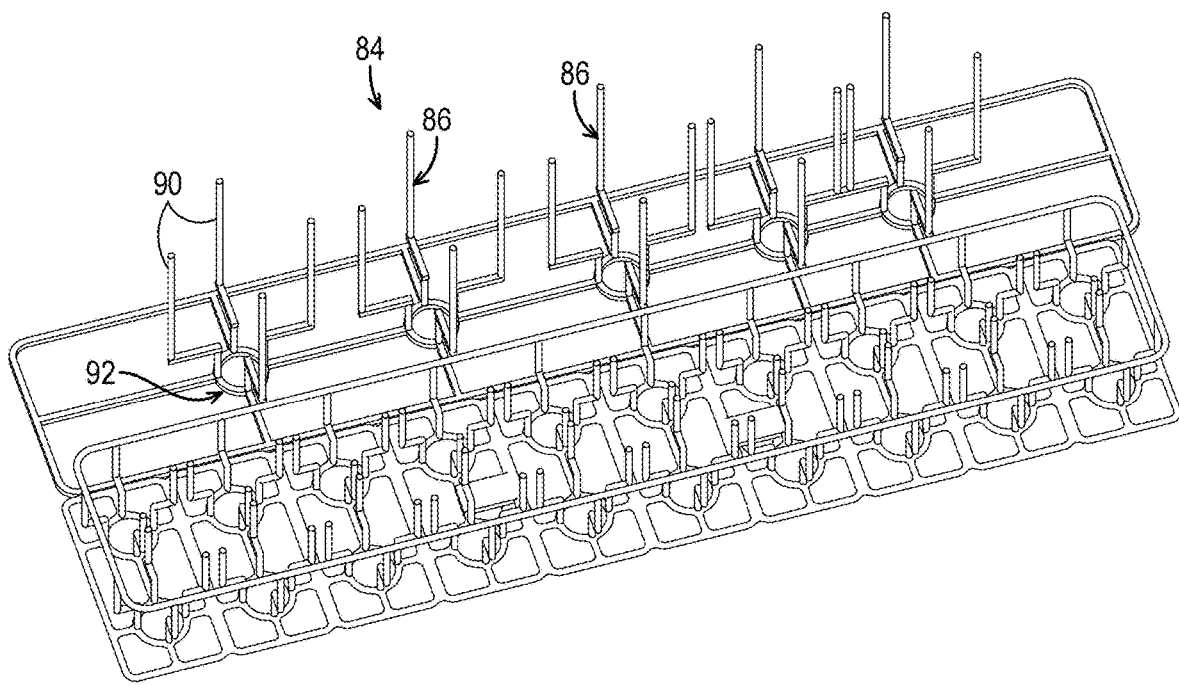
FIG. 3 is an isometric perspective view of a carrier for the sterility testing assembly of FIG. 2A.
Figure 4:
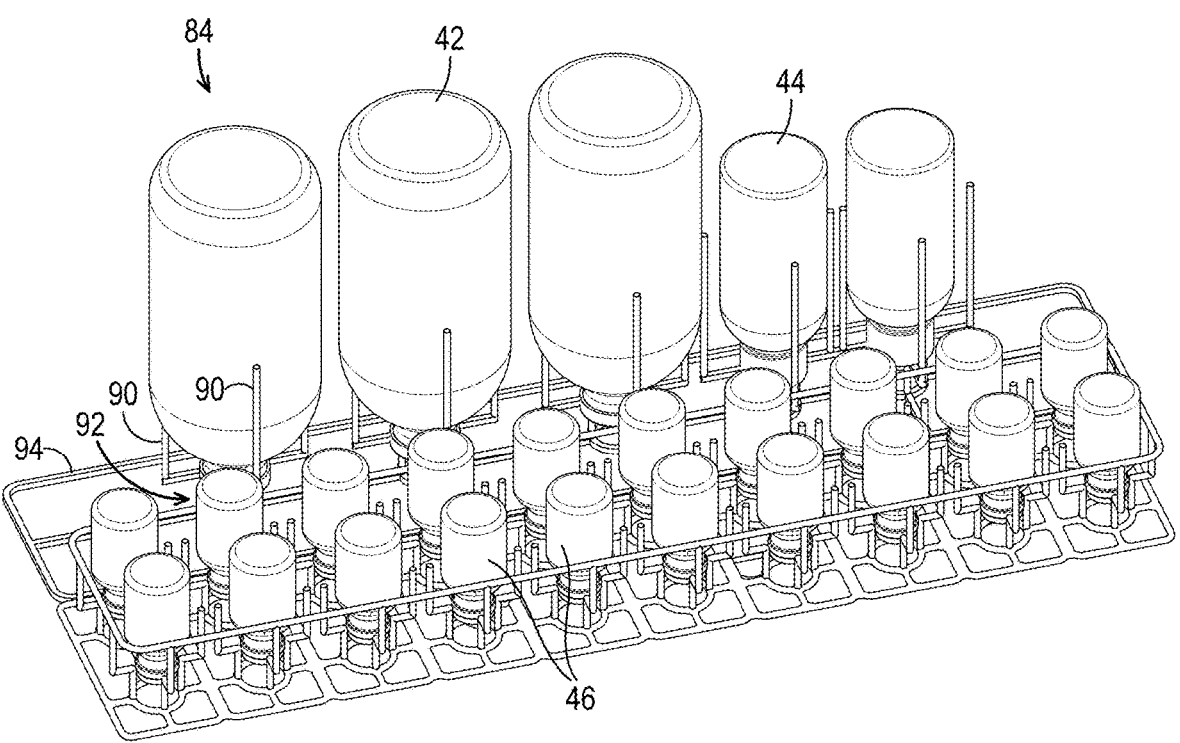
FIG. 4 is an isometric perspective view of the carrier with bottles disposed thereon.

Referring now to FIGS. 3 and 4, a carrier 84 (e.g., a wire rack or nest) of the test kit 32 and samples 46 is depicted as having multiple bottle or container retainers 86 sized and shaped to retain containers of the test kit 32 and samples 46 to be tested. In some embodiments, the containers in the test kit 32 and the samples 46 include containers with caps or other closures that are pierceable by the needle or ampoules with end portions that are pierceable by the needle. Each of the retainers 86 preferably has one or more prongs 90 designed to reduce contact with containers 42, 44, 46 compared to a holder that has continuous contact with such containers about their perimeters. In some embodiments, the prongs 90 are sized and shaped to extend along a height of the plurality of containers 42, 44, 46 with the at least three prongs 90 positioned to circumferentially surround a respective closure-receiving space 92 that is defined by the carrier 84 and that is configured to receive a closure 94 of a respective one of the containers in the retainers 86. The containers preferably include approximately three wetting fluid containers 42 of the kit 32, two growth media containers 44 of the kit 32, and a number of sample containers 46 for testing using the kit 32 as typically specified in a standard such as United States Pharmacopeia ("USP") VI Chapter 71, such as twenty. In some embodiments, each of the containers is positioned upside down in the carrier 84 such that the respective closure 94 or opening of each container faces a bottom of the carrier 84 with each closure 94 positioned in a respective closure-receiving space 92 of the respective retainer 86 and the prongs 90 positioned circumferentially about the respective container. The retainers 86 are preferably arranged in rows, such as three rows, with the wetting fluid containers 42 and growth media containers 44 of the kit 32 positioned in a first row and with the sample containers 46 arranged in the second and third rows (see FIG. 4). The retainers 86 preferably include retainers in a variety of sizes to accommodate different sizes or shapes of the containers. As depicted in FIGS. 3 and 4, the retainers 86 for the wetting fluid containers 42 are preferably larger than the retainers 86 for the growth media containers 44 and the sample containers 46 to accommodate the comparatively larger size of the wetting fluid containers 42. The retainers 86 for the growth media containers 44 are in some cases larger than the retainers 86 for the sample containers 46.

Figure 2C:
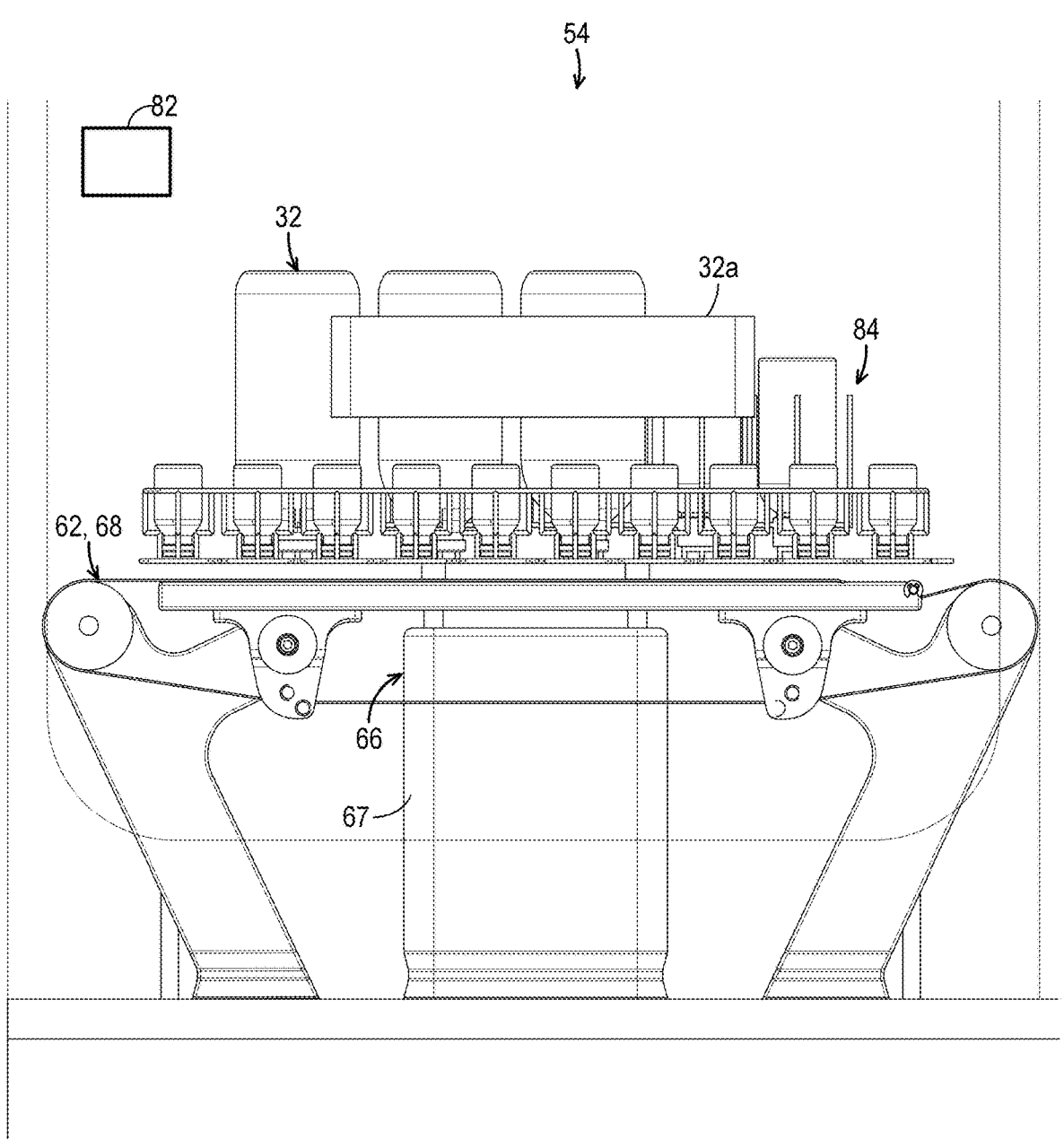
FIG. 2C is a front elevation view of an infeed pass chamber of the sterility testing assembly of FIG. 2A.

Referring now to FIG. 2C, the infeed pass chamber 54 is depicted as having a lifting platform 66 configured to lift the test kit 32 and samples 46 to be tested when the kit 32 and samples 46 are positioned on the conveyor 62 in the chamber 54. The conveyor 62 preferably has a pair of belts 68 (see FIG. 5) that are preferably each rotatable by one or more actuators for moving the pair of belts 68 along a length of the infeed pass chamber 54 out second door 60b. The pair of belts 68 are spaced apart from each other in a dimension perpendicular to their direction of travel to allow the lifting platform 66 to raise and lower between the pair of belts 68, thereby enabling the platform 66 to lift the carrier 84 of the test kit 32 and samples 46 off the conveyor 62 to more efficiently decontaminate the carrier 84, test kit 32, and samples 46. In particular, lifting the test kit 32 and samples 46 off the conveyor enables increasing the surface area of the test kit 32 and samples 46 that is exposed during decontamination. The lifting platform 66 preferably has a linear actuator 67 (such as a pneumatic cylinder or another pneumatic actuator) configured to lift the carrier 84, test kit 32, or samples 46. The infeed pass chamber 54 preferably has a decontamination assembly 82 configured to decontaminate the test kit 32 and samples 46, an interior of the infeed pass chamber 54, the conveyor 62, the lifting platform 66, and the carrier 84. The decontamination assembly 82 preferably has a reservoir, a pump, and a nozzle for spraying a decontaminating substance from the reservoir into the chamber 54. Following decontamination, the test kit 32, samples 46, and carrier 84 are then lowered back onto the conveyor 62 before transfer to the sterility testing chamber 56 by the conveyor 62 in the infeed pass chamber 54. Once moved into the testing chamber 56, the carrier 84 is positioned by the conveyor 62 in the testing chamber 56 in a predetermined position and secured to the conveyor 62 in the testing chamber 56 by a brace 118 (see FIG. 5).

Figure 8:
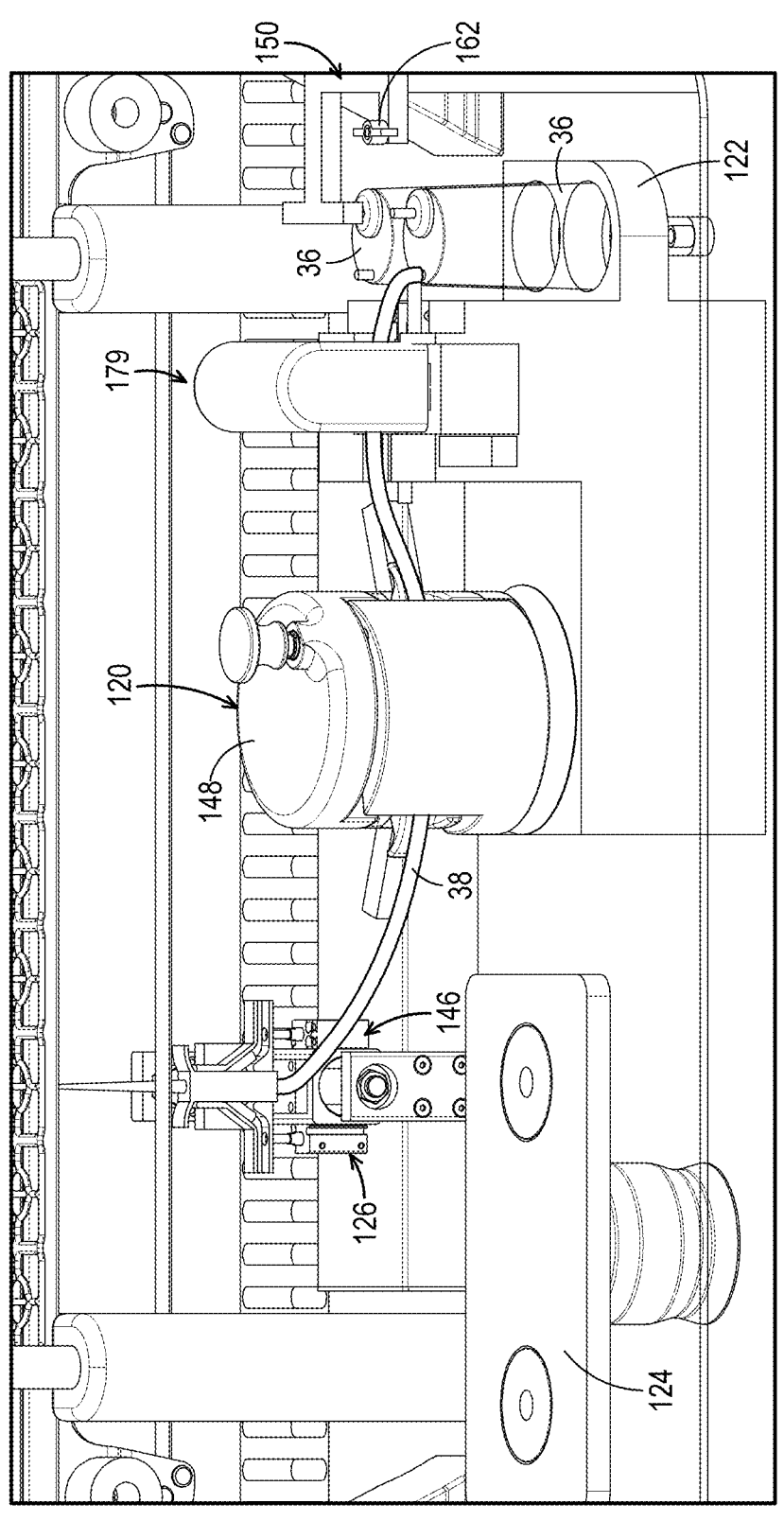
FIG. 8 is a partial front isometric perspective view of the sterility testing chamber of FIG. 5A.

When received at the location of the testing assembly 52, the test canisters 36, the first and second tubing 38, and the needle 34 of the kit 32 are preferably stored in a sterilized container 32a that is placed on the carrier 84 before decontamination in the infeed pass chamber 54 and subsequent movement into the testing chamber 56. Once in the chamber 56, an operator in some embodiments manipulates the sterilized container 32a, via gloves extending from a wall (not shown) of the testing chamber 56, to install the test canisters 36, the first and second tubing 38, and the needle 34 in the testing chamber 56, as shown in FIG. 8.

Referring now to FIG. 5, the testing chamber 56 is depicted before installation of the test canisters 36, the first and second tubing 38, and the needle 34. The testing chamber 56 has a conveyor 62, a brace 118, a tubing station 120, a test canister holder 122, a test kit opening station 124, and a needle control assembly 126. In some embodiments, the conveyor 62 in the testing chamber 56 is similar in structure to the conveyor 62 of the infeed pass chamber 54. The belts 68 of the conveyor 62 in the testing chamber 56 are preferably spaced apart a distance to enable the needle control assembly 126 to pass through between the belts 68 to pierce the closures of the containers in the carrier 84 with the needle 34. In particular, an outer perimeter of the carrier 84 is preferably positioned on the belts 68 so that the closures of the containers are exposed to the space between the belts 68.

The brace 118 is configured to brace the containers during piercing by the needle driven by the needle control assembly 126 to prevent lifting of the containers out of the carrier 84 by the needle or the needle control assembly 126. The brace 118 preferably has an actuator such as a linear actuator 119 that drives the brace 118 in a vertical direction to selectively contact the containers once the carrier 84 is positioned in a predetermined position on the conveyor 62 (see FIG. 13). In some embodiments, the profile of the lower surface of the brace 118 is shaped to complement or correspond to the upper profile of the wetting fluid containers 42, the growth media containers 44, and the sample containers 46 such that the lower surface of the brace 118 faces and simultaneously contacts the bottom of the wetting fluid containers 42, the growth media containers 44, and the sample containers 46. In some embodiments, the brace 118 is split into a plurality of portions, such as a first portion 118a, a second portion 118b, and a third portion 118c, where each portion contacts the containers of a respective row on the carrier 84. In this configuration, the brace 118 has a single linear actuator 119 that moves each of the portions of the brace 118 simultaneously. In some embodiments, the brace 118 includes two linear actuators that separately operate the brace 118 to independently and respectively contact the containers 42, 44 and the sample containers 46. As shown in FIG. 5, the first portion 118a has a lower surface that, in one section 121, matches the height of the containers 42 and, in another section 123, matches the height of the containers 44. The second and third portions 118b, 118c have lower surfaces that match the heights of the sample containers 46 containing the samples to be tested.

Figure 6:
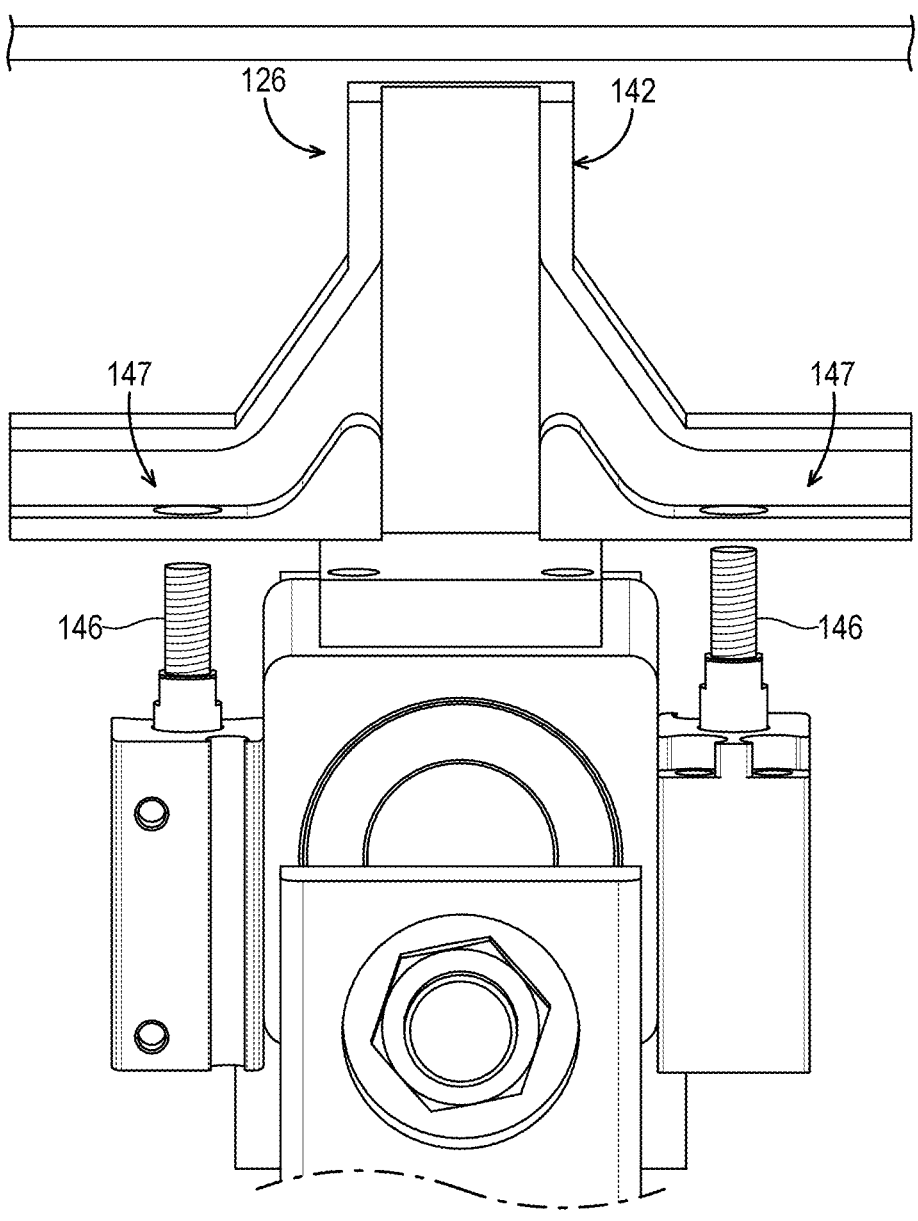
FIG. 6 is a front elevational view of a needle control assembly of the sterility testing assembly of FIG. 2A.

Referring to FIGS. 5A-5D and 6, the testing chamber 56 has the needle control assembly 126 positioned therein. The needle control assembly 126 has a needle holder 142 that is configured to selectively retain the needle 34 upon, in some embodiments, installation by the operator, while the sheath 144 remains on the needle 34. In some embodiments, the control assembly 126 has two pinch valves or pinchers 146 configured to selectively block fluid flow through the first and second tubing 38 when attached to the needle 34. The needle control assembly 126 is preferably coupled to a three-axis platform for moving the needle 34 along three axes each transverse to one another. The needle sheath 144 is configured to be separable from the needle 34 by moving the needle 34 or the sheath 144 away from one another. As shown in FIG. 6, the needle holder 142 has tube routing 147 for the first and second tubes 38 to extend from the needle 34 to the pinch valves 146. The pinch valves 146 preferably have actuators, such as linear actuators 149, that selectively drive the valves 146 into the routing 147 to selectively press the tubes 38, thereby selectively blocking fluid flow therethrough. In some embodiments, the operator installs the tubes 38 in the routing 147, thereby pairing each one of the pinch valves 146 with one of the first and second tubes 38 to enable the actuators to selectively block fluid flow through one of the first and second tubes 38 one at a time.

Figure 7:
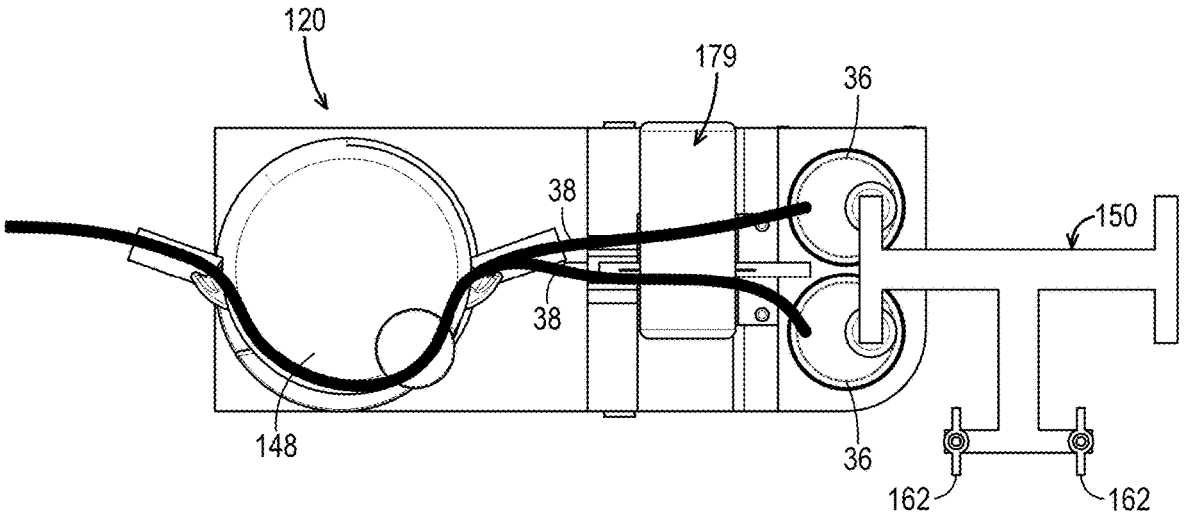
FIG. 7 is a top plan view of a tubing station for the sterility testing assembly of FIG. 2A.

Referring to FIGS. 7 and 8, the tubing station 120 preferably has a peristaltic liquid pump 148, the test canister holder 122 configured to hold the two test canisters 36, and a canister plug holding arm 150 configured to hold one or more canister plugs 162 and 39. In some embodiments, the first tubing 38 of the test kit 32 is installed by the operator to extend through the peristaltic liquid pump 148 such that actuation of the pump 148 moves fluid from the needle 34 to the respective test canisters 36.

Referring to FIGS. 9 through 12, the one or more canister plugs 162 and 39 on the canister plug holding arm 150 preferably has a pair of bottom plugs 162a and a pair of top plugs 162b. In some embodiments, the plugs 162 are part of the kit 32 and are provided in the container 32a, and the operator installs the plugs 162 on the holding arm 150 through the gloves. The top plugs 162a and the bottom plugs 162b are respectively attachable to the two test canisters 36 to seal the test canisters 36 before sending the test canisters 36 for testing of the sample fluid contained therein. The canister plug holding arm 150 has a sealing pad 164 configured to seal respective vent ports 170 on each of the test canisters 36, whereby sealing of the vent ports 170 controls fluid flow through the test canisters 36. The sealing pad 164 may be a single unitary piece that extends between the vent ports 170 on the test canisters 36, and may alternatively be separated into two separate portions that individually contact one of the vent ports 170 on the test canisters 36. Sealing the vent ports 170 enables a vacuum generated by the pump 177 to draw fluid through the filters 37 while sucking fluid through the tubes 38. Unsealing the vent ports 170 enables the pump 177 to empty the test canisters 36. Preferably, each test canister 36 has a fluid inlet 166 and a fluid outlet 39 in addition to the vent port 170, where fluid flow from the fluid inlet 166 through the fluid outlet 39 depends on whether the vent port 170 is sealed. The fluid inlet 166 is configured to allow liquid into the test canister, and the fluid outlet 39 is configured to drain liquid from the test canister. Each sealing pad 164 extends a length to be able to contact and seal the respective vent port 170 on each of the two test canisters 36 preferably simultaneously. The holding arm 150 preferably has an actuator 151 configured to move the sealing pad 164 into and out of contact with the vent ports 170 of the one or more test canisters 36. In some embodiments, the actuator translates the holding arm 150 vertically to selectively seal the vent ports 170.

Referring to FIGS. 11 and 12, the test canisters 36 are depicted with a drain assembly 172 that drains fluid from the test canisters 36. The drain adaptor 174 is preferably configured to selectively connect to the fluid outlet 39 to permit draining of fluid from the one or more test canisters 36 through the fluid outlet 39, whereby the selective connection of the drain adaptor 174 to the fluid outlet 39 of the one or more test canisters 36 permits selective draining of fluid from the one or more test canisters 36. The drain adaptor 174 preferably extends between the two test canisters 36 to selectively connect to the fluid outlet 39 of each of the two test canisters 36. The drain assembly 172 has a drain adaptor 174 with an actuator 175 configured to move the drain adaptor 174 into and out of contact with the fluid outlets 39 to selectively connect the drain adaptor 174 to the fluid outlets 39 and a pump 177 downstream of the adaptor 174 to be configured to draw fluid through the drain adaptor 174.

Referring to FIGS. 1 through 13, the assembly 52 has a controller 176 operatively or communicably coupled to and configured to control one or more of: the needle control assembly 126, the drain assembly 172, the peristaltic liquid pump 148, the canister plug holding arm 150, the conveyors 62, and the brace 118 during operation. The controller 176 sends one or more signals that cause one or more of the needle to move to the next of the containers on the carrier 84 or to activate and deactivate the pump 148 after piercing each container to selectively drain a fluid from each of the containers to the test canisters 36. The controller 176 preferably has a preprogrammed or stored location for each of the containers when the conveyor 62 stops and thus the carrier 84 is in the predetermined position shown in FIG. 13, along with a predetermined path for moving the needle between each container in a desired order (see FIG. 13). When the needle is moved to one of the containers, the needle is preferably positioned below the container with the needle aligned with the closure 94 of the container before the controller 176 sends a signal to cause the needle to move vertically to pierce the cap or other closure. The pump 148 is then activated to move fluid from the pierced container to the test canister 36. The controller 176 is configured to send one or more signals to cause the holding arm 150 to unseal the vent ports 170 before activating the pump 177 downstream of the canisters 36. After draining the container, the pump 148 is deactivated and the needle is moved vertically away from the container to remove the needle from the container. The controller 176 then causes the needle to move to the next container in the predetermined path, as shown in FIG. 13.

To selectively fill each of the test canisters 36, the controller 176 activates the pinch valves 146 individually when the needle is moved along the predetermined path. In some embodiments, the controller 176 may activate the pinch valve 146 to close the tubing that extends from the needle to the aerobic test canister, then move the needle through the predetermined path to fill the anaerobic test canister with fluid from the samples and the anaerobic growth media. The controller 176 may then activate the pinch valve 146 to close the tubing that extends from the needle to the anaerobic test canister and deactivate the pinch valve 146 for the aerobic test canister, then move the needle through the predetermined path to fill the aerobic test canister with fluid from the samples and the aerobic growth media.

In operation, the operator may insert the carrier 84 with the plurality of containers and the test kit 32 through the door 60 in the infeed pass chamber 54 to place the carrier 84 on the conveyor 62. The controller 176 may then send one or more signals to cause one or more of: the door to close; the lifting platform 66 to lift the carrier 84 off of the conveyor; or the decontamination assembly 82 to decontaminate the carrier 84 and its contents, including the sample containers and the test kit container 32a and chamber 54. Following decontamination, the controller 176 may send one or more signals to cause one or more of: the lifting platform 66 to return the carrier 84 to the conveyor 62; the door 60 between the infeed pass chamber 54 and the testing chamber 56 to open; or activate the conveyors 62 of the infeed pass chamber 54 and the testing chamber 56 to move the carrier 84 into position in the testing chamber 56.

Once the carrier 84 is positioned in the testing chamber 56, the operator may extend their hands through gloves (not shown) to install the test kit 32 in the test kit opening station 124. Suction from the opening station 124 retains the test kit container 32a in position while the operator opens the test kit container 32a. The operator may then install one or more of the test canisters 36, the tubing 38, the needle 34, or the closures 162 for the test canisters 36. Following installation, the controller 176 activates the brace 118 to retain the containers in position on the carrier 84, as shown in FIGS. 5 and 13. The controller 176 may then send one or more signals to cause one or more of the needle control assembly 126 to remove the needle from the sheath 144 by moving the needle and the sheath 144 away from one another or to move the needle to puncture the closure 94 of one of the wetting fluid containers 46. The controller 176 then activates the pump 148 to load the wetting fluid into the test canisters 36. The controller 176 further activates the pump 177 in the drain assembly 172 to drain the wetting fluid through the filter 37 in the test canisters 36 and out of the fluid outlet 39 while the vent port 170 is unsealed.

Following wetting of the filter in the test canisters 36, the controller 176 sends one or more signals that move the needle holder 142 to pierce and drain the fluid from the sample containers to move the sample fluid through the filter in the test canisters 36. Once the sample containers are drained, the controller 176 then deactivates the pump 177 of the drain assembly 172 and actuates the actuator of the canister plug holding arm 150 to unseal the vent port 170 on the test container. The controller 176 then initiates filling the test canisters 36 with the fluid from one of the anaerobic growth media and the aerobic growth media. To fill the test canisters 36 separately with the aerobic and anaerobic growth media, the controller 176 activates the pincher 146 to pinch the second tubing 38 extending to the second test container 36 and moves the needle holder 142 to pierce the aerobic growth media container 46 with the needle and fill the first test container 36 with the aerobic growth media 46 with the vent port 170 unsealed. After draining the aerobic growth media bottle 44, the pincher 146 releases the second tubing 38 and pinches the first tubing 38 to drain the fluid from the anaerobic growth media 44 container to the second test container 36 with the vent port 170 unsealed.

After filling the two test canisters 36 with the aerobic growth media and the anaerobic growth media, respectively, the needle may be moved into the sheath 144 by aligning the needle with a cavity of the sheath 144 and moving the needle toward the sheath 144. Prior to adding the media to the canisters 36, however, the drain adapter or port 174 is removed from the fluid outlets 39 of the test canisters 36 by actuating the actuator 175 of the drain assembly 172 to allow the actuator arm 150 to insert the bottom plugs 162a into the fluid outlets 39. The actuator arm 150 additionally inserts the top plugs 162b into the open vent ports 170 on the test canisters 36.

FIGS. 14A-16 show the system 52 including a sealing-and-cutting station 179 with an actuator 180, a sealer 181, a blade 182, and another actuator 183 according to some embodiments. The blade 182 preferably includes a scalpel or razor blade that is configured to cut the tubing 38 extending between the needle holder 142 and the test canisters 36. The sealer 181 preferably includes a heat sealer, ultrasonic welder, or other sealer configured to seal the tubing 38 at a median portion between the needle holder 142 and the test canisters 36. In some embodiments, the sealer 181 includes sealing elements on opposing sides of the blade 182 to create a seal in the tubing 38 on each side of the blade 182. In some embodiments, the sealing elements are integrated together as a single element. Sealing of the tubing 38 extending to the test canisters 36 are created to create a seal on the fluid inlet 166 and to dispose of the tubing 38 prior to a new cycle of sterility testing. As shown in FIGS. 15 and 16, the sealing-and-cutting station 179 includes a pair of tube holders such as channels 184 sized and dimensioned to retain the tubing 38. Actuation of the actuator 183 lowers the blade 182 into contact with the tubing 38 held in the holders 184 to slice both tubings 38 simultaneously. In a preferred embodiment, the actuator 180 is configured to translate or move the sealer 181 into contact with the tubing 38 to heat seals each of the first tubing 38 and the second tubing 38 in two places. Following operation of the actuator 180, the actuator 183 is operated to lower the blade 182 into contact with the tubing 38 to cut the first and second tubing 38 between the sealed portions of the tubing 38. In some embodiments, this process is activated by the controller 176 once the test canisters 36 are filled with the growth media 44. Following cutting of the tubes 38, the controller 176 preferably sends one or more signals to release the brace or move the test kit 32 to the outfeed pass chamber via the conveyors. The operator may then remove the test kit 32 and the filled test canisters 36.

The tubing 38 shown in the Figures is a schematic representation of the orientation and fluid coupling provided by the tubing 38. In practice, the tubing 38 shown in FIG. 16 preferably extends to the needle and the inlet ports of the test containers 36. Preferably, the tubing 38 being disposed in the tube holders 184 positions the tubing 38 relative to the blade 182 such that the different edges of the blade 182 cut the respective pieces of tubing 38 that are in the different tube holders 184, as shown in FIG. 14B without the tube holders 184 for increased visibility of the blade 182.

As used herein, a "controller" may include one or more processors and one or more memories for performing the functions or actions described herein. The one or more processors are preferably in communication with the one or more memories via a bus. Additionally, the one or more memories preferably include data storage, which stores the instructions for the one or more processors to send signals for performing the functions or actions described herein.

The term "configured" as used herein means an element being one or more of sized, dimensioned, positioned, or oriented to achieve or provide the recited function or result. The term "coupled" should be understood to disclose both direct and indirect coupling of components or elements that are described as being coupled to each other.

The term "or" is an inclusive grammatical conjunction to indicate that one or more of the connected terms may be employed. For example, the phrase "one or more A, B, or C" or the phrase "one or more As, Bs, or Cs" is employed to discretely disclose each of the following: i) one or more As, ii) one or more Bs, iii) one or more Cs, iv) one or more As and one or more Bs, v) one or more As and one or more Cs, vi) one or more Bs and one or more Cs, and vii) one or more As, one or more Bs, and one or more Cs. The term "based on" as used herein is not exclusive and allows for being based on additional factors not described. The articles "a," "an," and "the" have plural references. Plural references are intended to also disclose the singular.

The term "transverse" is used herein to describe the orientation of the features herein as not parallel to.

While the preferred embodiment of the invention has been illustrated and described, as noted above, many changes can be made without departing from the spirit and scope of the invention. Each disclosure of a component preferably having a feature or characteristic is intended to also disclose the component as being devoid of that feature or characteristic, unless the principles of the invention clearly dictate otherwise. Accordingly, the scope of the invention is not limited by the disclosure of the preferred embodiment. Instead, the invention should be determined entirely by reference to the claims that follow. It should also be noted that the claim dependencies or combinations of elements recited in the claims do not reflect an intention to forgo claiming other subject matter disclosed herein. Instead, this disclosure is intended to also disclose the subject matter of any combination of any two or more of the claims, such that subsequent claim sets may recite that any one of the dependent claims depends from any other one or more claims, up to and having all other claims in the alternative (such as "The apparatus or method of any one of the preceding or subsequent claims . . . "). This disclosure is also intended to disclose the subject matter of any one of the dependent claims, as if it were an independent claim, with or without all or a portion of the subject matter of the original independent claim(s) or any other subject matter disclosed herein.

Those of ordinary skill in the art will conceive of other alternate embodiments of the invention upon reviewing this disclosure. Thus, the invention is not to be limited to the above description but is to be determined in scope by the claims that follow.

The invention claimed is:

1. An automated sterility testing assembly for testing sterility of pharmaceutical fluids, the assembly comprising:
   a needle holder configured to selectively retain a needle fluidly coupled to a sterility testing filter, the holder being configured to move the needle in a first direction to pierce a selected one of respective closures of a plurality of fluid containers disposed on a carrier, the holder being configured to move the needle in a second direction opposite the first direction to remove the needle from the selected one of the respective closures;
   at least one pump of a set of one or more pumps, the at least one pump being configured to draw fluid through the selected one of the respective closures through a filter in a test container after the needle pierces the selected one of the respective closures and before the needle is removed from the selected one of the respective closures, the test container being configured to receive pharmaceutical fluid and bacterial growth media to facilitate testing sterility of the pharmaceutical fluid;
   a brace sized and dimensioned to brace the plurality of fluid containers during piercing the respective closures by the needle,
   whereby the brace prevents the needle from moving the plurality of fluid containers out of the carrier;
   a vent seal actuator configured to selectively seal with a vent sealer a vent port of the test container during filling of the test container with liquid from one or more of the fluid containers or draining the liquid from the test container;
   a tube sealer configured to seal a median portion of a tubing extending between the needle holder and the test container; and

a cutter configured to cut the tubing at a location between the median portion and the needle holder, whereby sealing and cutting of the tubing enables removal of the test container while contents of the test container are sealed.

2. The testing assembly of claim 1, further comprising a plug holding arm configured to selectively hold a plug for the test container, the plug holding arm being configured to insert the plug into the vent of the test container after draining the growth media from a container of the plurality of fluid containers into the test container, the plug holding arm being configured to release the plug after inserting the plug into the vent of the test container.

3. The testing assembly of claim 1, further comprising a plug holding arm configured to selectively hold a plug for the test container, the plug holding arm being configured to insert the plug into a fluid outlet of the test container before draining the bacterial growth media from a container of the plurality of fluid containers into the test container, the plug holding arm being configured to release the plug after inserting the plug into the fluid outlet of the test container.

4. The testing assembly of claim 1, further comprising one or more processors having memory, the memory storing instructions, the one or more processors being configured to execute the instructions stored by the memory, the instructions, when executed by the one or more processors, causing:

the at least one pump of the set of one or more pumps to draw the pharmaceutical fluid from a first container of the plurality of containers into the test container;

the one or more processors to determine that one or more pumps of the set of one or more pumps are finished drawing the pharmaceutical fluid out of the test container; and the at least one pump of the set of one or more pumps to draw a rinsing fluid from a second container of the plurality of containers into the test container based on the one or more processors determining that the one or more pumps of the set of one or more pumps finished drawing the pharmaceutical fluid out of the test container.

5. The testing assembly of claim 1, further comprising:

a conveyor configured to move the carrier in the assembly; and a vertical actuator configured to lift the carrier off the conveyor during a decontamination process.

6. The testing assembly of claim 1, further comprising a drain actuator configured to selectively couple a drain adaptor to a fluid outlet of the test container to enable one or more pumps of the set of one or more pumps to drain the liquid from the test container through the fluid outlet and to enable coupling a plug to the fluid outlet of the test container after separation of the drain adapter from the fluid outlet.

7. An automated sterility testing assembly for testing sterility of pharmaceutical fluids, the assembly comprising:

a needle holder configured to selectively retain a needle fluidly coupled to a sterility testing filter, the holder being configured to move the needle in a first direction to pierce a selected one of respective closures of a plurality of fluid containers disposed on a carrier, the holder being configured to move the needle in a second direction opposite the first direction to remove the needle from the selected one of the respective closures;

a pump configured to draw fluid through the selected one of the respective closures and through a filter in a test container after the needle pierces the closure, the test container being configured to receive pharmaceutical liquid and bacterial growth media to facilitate testing sterility of the pharmaceutical liquid; and a brace sized and dimensioned to brace the plurality of fluid containers during piercing of the respective closures by the needle, whereby the brace prevents the needle from moving the plurality of fluid containers out of the carrier.

8. The testing assembly of claim 7, further comprising:

a conveyor configured to move the carrier in the assembly; and a vertical actuator configured to lift the carrier off the conveyor during a decontamination process.

9. The testing assembly of claim 8, wherein the carrier has a plurality of retainers sized and dimensioned to retain the plurality of fluid containers, each of the plurality of retainers having one or more prongs sized and dimensioned to provide reduced contact with the plurality of fluid containers compared to a holder that provides contact with a continuous region of each of the plurality of fluid containers about perimeters of the plurality of fluid containers.

10. The testing assembly of claim 9, wherein the one or more prongs of each of the retainers include at least three prongs spaced apart to circumferentially surround a respective one of closure-receiving spaces defined by the carrier, the closure-receiving spaces being sized and dimensioned to receive respective ones of the respective closures of the plurality of fluid containers, the needle holder being configured to move the needle to pierce the selected one of the respective closures while the selected one of the respective closures is disposed in one of the closure-receiving spaces.

11. The testing assembly of claim 9, wherein the plurality of retainers is arranged in at least one row and a plurality of columns, and the needle holder is configured to move the needle into the closure-receiving spaces in a predetermined order.

12. The testing assembly of claim 7, wherein the brace is sized and shaped to complement a profile defined by the fluid containers such that the brace simultaneously contacts each of the fluid containers.

13. The testing assembly of claim 7, wherein the brace is configured to contact the plurality of fluid containers before the needle holder moves the needle to pierce the selected one of the respective closures.

14. The testing assembly of claim 7, further comprising a pincher configured to selectively restrict fluid flow through tubing fluidly coupling the needle and the test container.

15. The testing assembly of claim 7, further comprising:

a tube sealer configured to seal a median portion of a tubing fluidly coupling the needle holder and the test container; and a cutter configured to cut the tubing at a location along a length of the tubing between the median portion and the needle holder, whereby sealing and cutting of the tubing enables removal of the test container while contents of the test container are sealed.

16. A method for automated sterility testing of pharmaceutical fluids, the method comprising:

moving a brace in a first direction into contact with a plurality of containers to restrain the plurality of containers in a carrier holding the plurality of containers;

moving a needle in a second direction opposite the first direction to pierce a closure of a first container of the plurality of containers;

activating a pump to drain fluid from the first container into a first test container;

moving the needle in the second direction to remove the needle from the closure of the first container;

moving the needle in a third direction transverse to the first direction to position the needle under to a second container of the plurality of containers; and moving the needle in the second direction to pierce a closure of the second container, whereby the brace prevents the needle from moving containers being pierced by the needle out of the carrier.

17. The method of claim 16, wherein the first container contains a filter wetting fluid, and the second container contains the pharmaceutical liquid to be tested.

18. The method of claim 17, further comprising:

moving the needle with an actuator to pierce a rinsing-fluid container;

draining, through the needle and from the rinsing-fluid container, a rinsing fluid into the first test container after drawing the pharmaceutical liquid from the second container into the first test container;

after the draining of the rinsing fluid, moving the needle with an actuator to pierce a growth-media container that contains the growth media; and draining, through the needle and from the growth-media container, the growth media into the first test container.

19. The method of claim 16, wherein the first container contains the pharmaceutical liquid to be tested and the second container contains the growth media, the growth media including an aerobic or anaerobic growth media.

20. The method of claim 16, further comprising:

pinching with an actuator first tubing that fluidly couples the needle to the first test container and thereby restricting fluid flow from the second container to the first test container; and pumping, through the needle and while the first tubing is pinched, fluid from the second container to a second test container.

21. The method of claim 20, further comprising:

un-pinching with the actuator the first tubing and thereby enabling flow from the second container to the first test container;

pinching with an actuator the second tubing and thereby restricting fluid flow from the second container to the second test container; and pumping, through the needle and while the second tubing is pinched, fluid from the second container to the first test container.

22. The method of claim 20, further comprising:

unsealing with an actuator a vent port of the first test container; and filling the first test container with the growth media while the vent port is unsealed.

23. The method of claim 22, further comprising attaching with a plug holding arm a plug to the vent port of the first test container after filling the first test container with the growth media.

24. The method of claim 16, further comprising:

sealing a median portion of a tubing fluidly coupling the needle and the first test container; and cutting the tubing between the needle and the median portion, whereby sealing and cutting of the tubing enables removal of the first test container while contents of the first test container are sealed.

25. The method of claim 16, further comprising:

raising the carrier via an actuator; and decontaminating, while the fixture is raised, the carrier and the plurality of containers.

26. The method of claim 16, further comprising removing a sheath from the needle before piercing one of the plurality of containers.

* * * * *